(12) United States Patent
Chun et al.

(10) Patent No.: US 9,447,457 B2
(45) Date of Patent: Sep. 20, 2016

(54) DETECTION OF TARGET NUCLEIC ACID SEQUENCES BY CYCLIC EXONUCLEOLYTIC REACTIONS

(75) Inventors: Jong Yoon Chun, Seoul (KR); In Taek Hwang, Seoul (KR)

(73) Assignee: SEEGENE, INC., Seoul (KR)

( * ) Notice: Subject to any disclaimer, the term of this patent is extended or adjusted under 35 U.S.C. 154(b) by 0 days.

(21) Appl. No.: 13/497,310

(22) PCT Filed: Apr. 9, 2010

(86) PCT No.: PCT/KR2010/002209
§ 371 (c)(1),
(2), (4) Date: Apr. 5, 2012

(87) PCT Pub. No.: WO2011/037306
PCT Pub. Date: Mar. 31, 2011

(65) Prior Publication Data
US 2012/0190030 A1     Jul. 26, 2012

(30) Foreign Application Priority Data

Sep. 24, 2009  (KR) .................. 10-2009-0090710
Oct. 28, 2009  (KR) .................. 10-2009-0103082

(51) Int. Cl.
*C12Q 1/68*     (2006.01)

(52) U.S. Cl.
CPC ..................................... *C12Q 1/682* (2013.01)

(58) Field of Classification Search
None
See application file for complete search history.

(56) References Cited

U.S. PATENT DOCUMENTS 5,573,907 A   11/1996   Carrino et al.

FOREIGN PATENT DOCUMENTS

| EP | 0578138 A2 | 1/1994 |
|---|---|---|
| JP | H06500021 A | 1/1994 |
| JP | H0630799 A | 2/1994 |
| WO | WO-92/02638 A1 | 2/1992 |
| WO | WO 2008/011004 A2 | 1/2008 |

OTHER PUBLICATIONS

Clarke et al., Nature Nanotechnology, 2009, vol. 4, pp. 265-270.*
Shevelev et al., Nature Reviews Molecular Cell Biology, 2002, vol. 3, pp. 1-12.*
Higuchi et al., Biotechnology, 1993, vol. 11, pp. 1026-1030.*
Ginzinger, Experimental Hematology, 2002, vol. 30, pp. 503-512.*
IDT Manual, Strategies for Attaching Oligonucleotides to Solid Supports, 2005, pp. 1-22.*
Larsson et al., "In Situ Genotyping Individual DNA Molecules by Target-Primed Rolling Circle Amplification of Padlock Probes," Nature Methods 1:227-232, 2004.
Wang et al., "Exonuclease III Protection Assay with FRET Probe for Detecting DNA-Binding Proteins," Nucleic Acids Res. 33:1-9, 2005.
International Search Report from PCT/KR2010/002209 dated Jan. 28, 2011 (date of mailing of report) and Jan. 27, 2011 (date of completion of search).
Arya et al., "Basic principles of real-time quantitative PCR," Expert Rev Mol Diagn. 5(2):1-11 (2005).
Gibson et al., "A novel method for real time quantitative RT-PCR," Genome Res. 6(10):995-1001 (1996).
Heid et al., "Real time quantitative PCR," Genome Res. 6(10):986-94 (1996).
Office Action for Japanese Application No. JP 2015-036458, dated Feb. 2, 2016 (12 pages).

* cited by examiner

*Primary Examiner* — Michele K Joike
*Assistant Examiner* — Mindy G Brown
(74) *Attorney, Agent, or Firm* — Clark & Elbing LLP; Susan M. Michaud

(57) ABSTRACT

The present invention relates to the detection of a target nucleic acid sequence by a cyclic exonucleolytic reaction. The present method enabling to generate signals by probe digestion with no help of primers and to amplify signals with no help of simultaneous target amplification reactions may enable to detect multiple target sequences without any problems accounted in the conventional real-time PCR methods such as false positive signals and difficulties in oligonucleotides (primer and probe) selection and reaction condition optimization.

6 Claims, 16 Drawing Sheets

Fig. 1a
(a) Hybridization
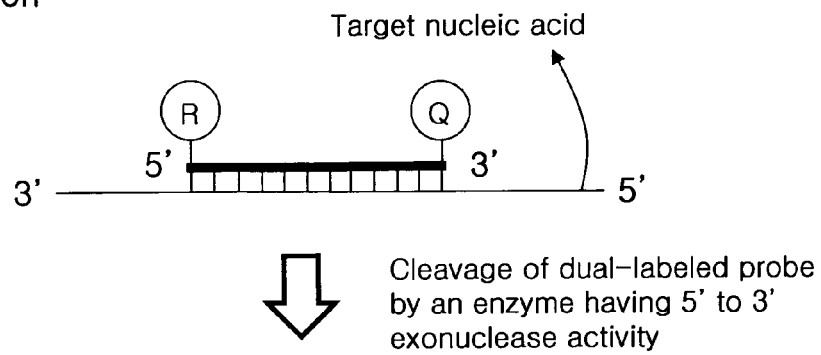
Cleavage of dual-labeled probe by an enzyme having 5' to 3' exonuclease activity
(b) Generation of target signal
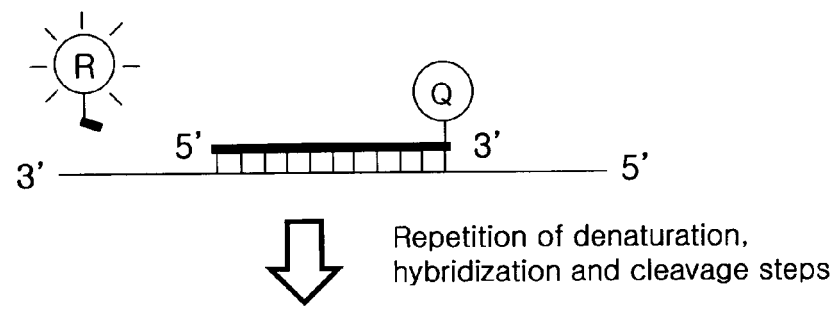
Repetition of denaturation, hybridization and cleavage steps
(c) Amplification of target signal
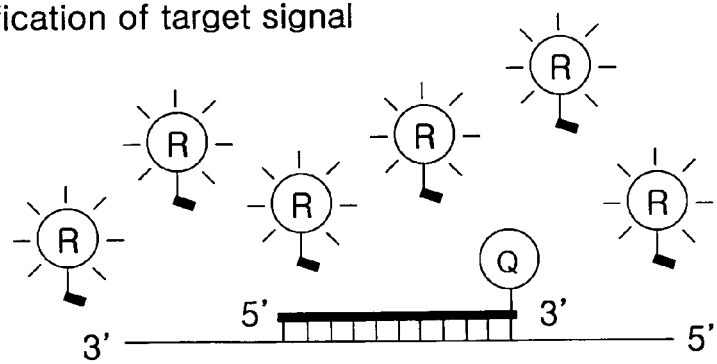
(R) : Reporter molecule    (Q) : Quencher molecule

Fig. 1b
(a) Hybridization
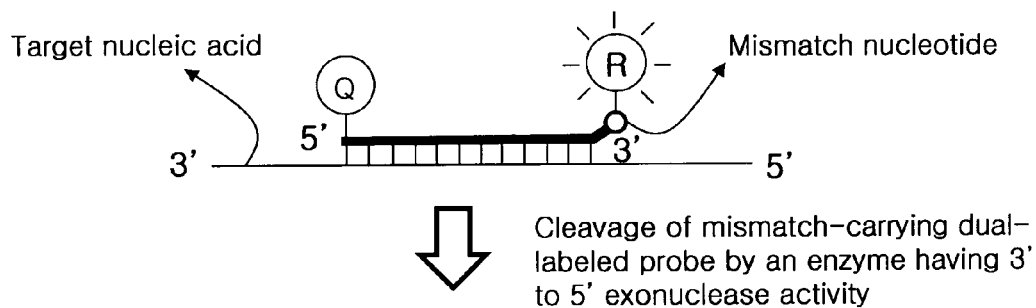
Cleavage of mismatch-carrying dual-labeled probe by an enzyme having 3' to 5' exonuclease activity
(b) Generation of target signal
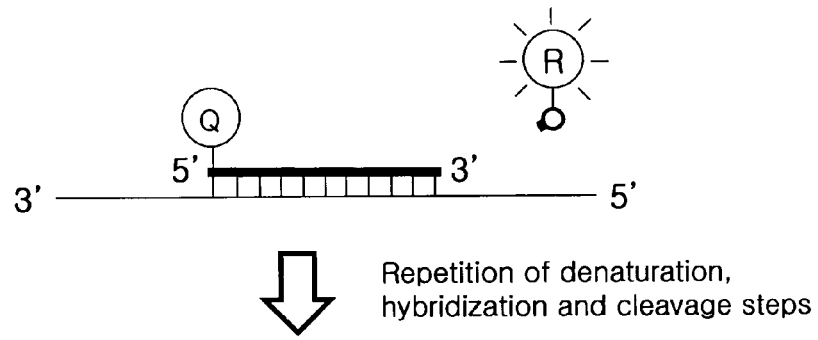
Repetition of denaturation, hybridization and cleavage steps
(c) Amplification of target signal
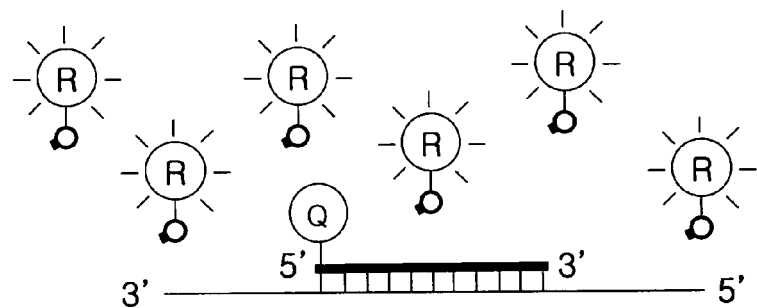
(R) : Reporter molecule        (Q) : Quencher molecule

Fig. 2a
(a) Pre-amplification
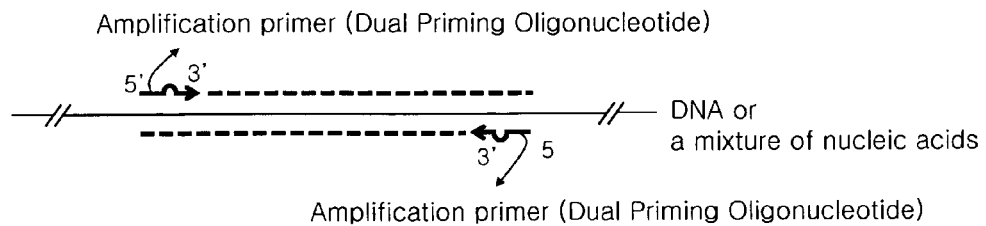
(b) Hybridization
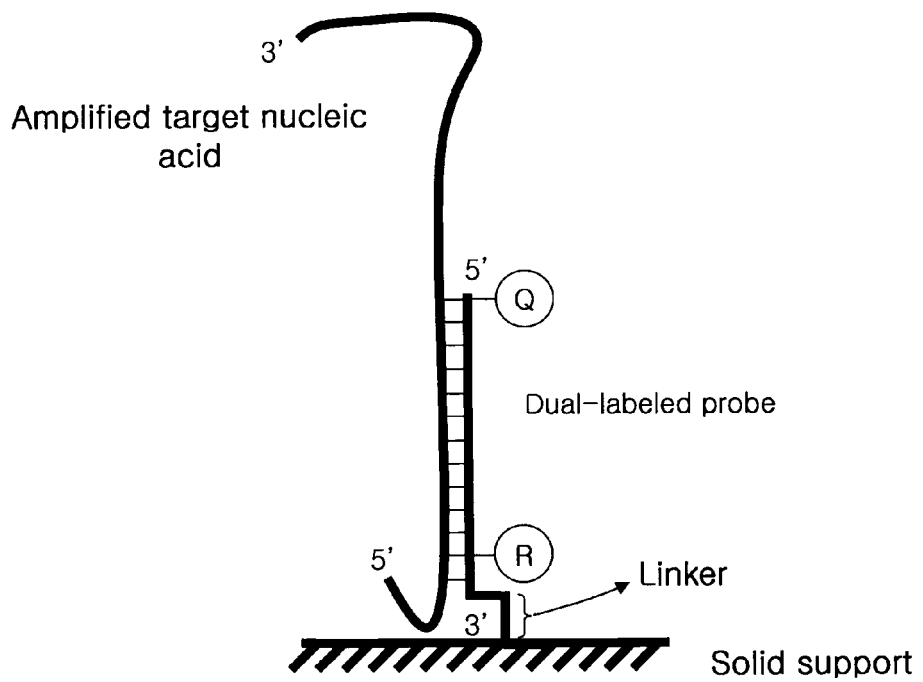

(c) Generation of target signal

Cleavage of dual-labeled probe by an enzyme having 5'→3' exonuclease activity and signal generation Solid support ⇩ Repetition of denaturation, hybridization and cleavage steps (d) Amplification of target signal (R) : Reporter molecule        (Q) : Quencher molecule

Fig. 3a
(a) Pre-amplification
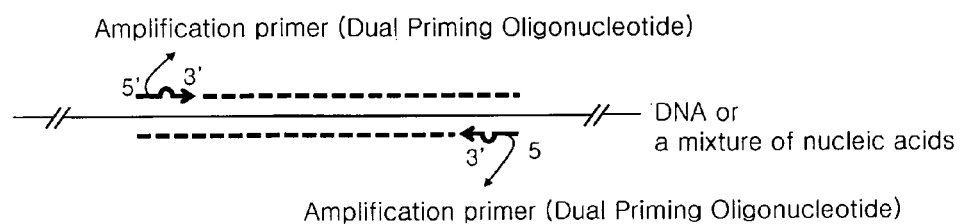
(b) Hybridization
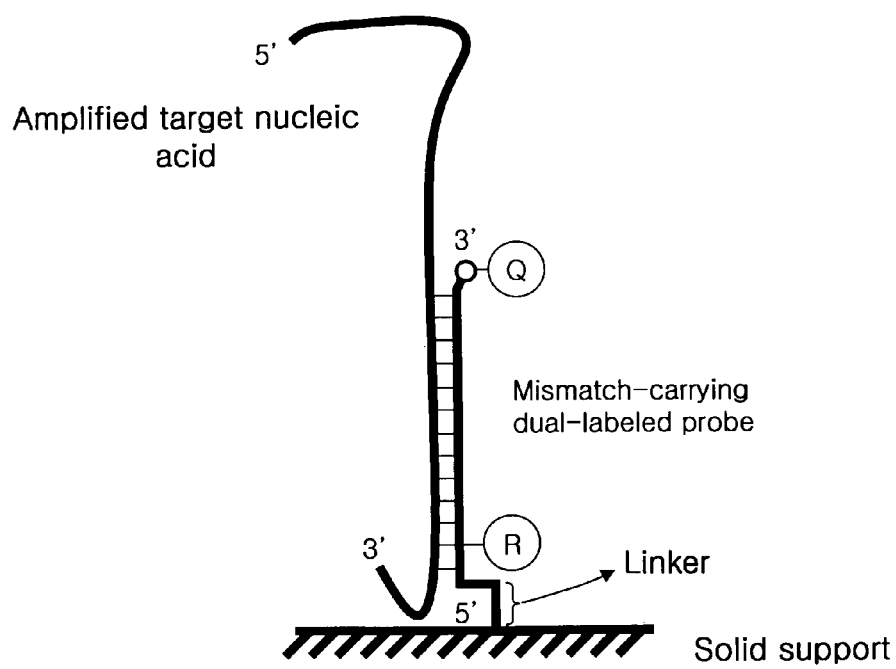
○ : Mismatch nucleotide (c) Generation of target signal Cleavage of mismatch-carrying dual-labeled probe by an enzyme having 3'→5' exonuclease activity and signal generation Repetition of denaturation, hybridization and cleavage steps (d) Amplification of target signal

- (R) : Reporter molecule
- (Q) : Quencher molecule
- O : Mismatch nucleotide (a) Hybridization

Fig. 5

Cleavage of dual-labeled probe independent on interaction with primer or extended product of the primer (a) 5'-3' nuclease activity independent on interaction with primer:
No binding of primer to target nucleic acid

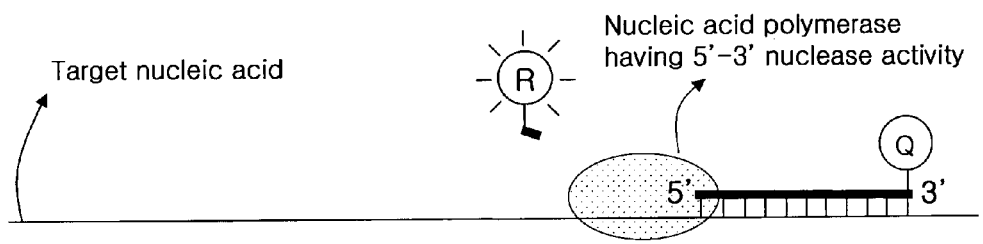

(b) 5'-3' nuclease activity independent on interaction with primer:
Binding of primer to target nucleic acid but no interaction between the primer and the polymerase on the probe

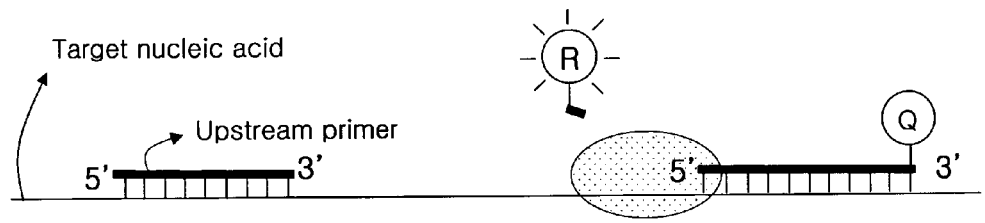

(c) 5'-3' nuclease activity independent on interaction with extended product of primer: Extension of primer but no interaction between the extended product and the polymerase on the probe

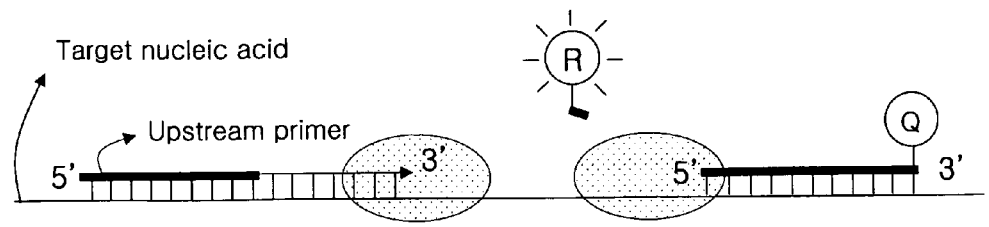

( R ) : Reporter molecule      ( Q ) : Quencher molecule

Fig. 6

Cleavage of dual-labeled probe dependent on interaction with primer or extended product of the primer (a) 5'-3' nuclease activity dependent on interaction with primer: polymerization-independent activity

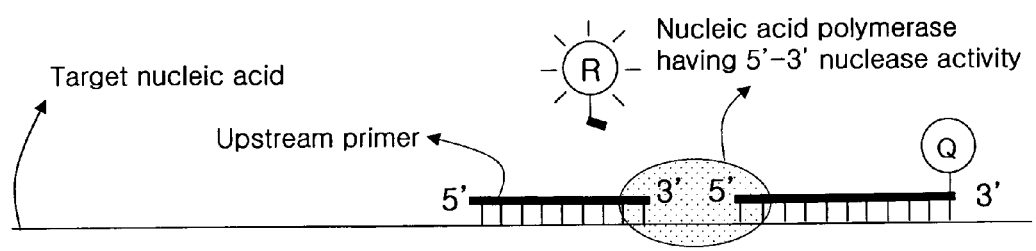

(b) 5'-3' nuclease activity dependent on interaction with extended product of primer: polymerization-dependent activity

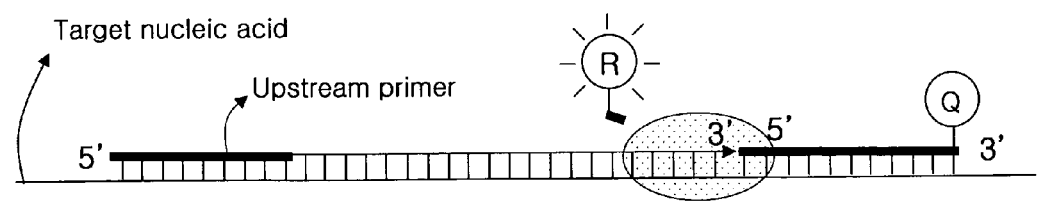

(R) : Reporter molecule    (Q) : Quencher molecule

Fig. 7

Real-time simultaneous dual-signal amplification (a) Hybridization

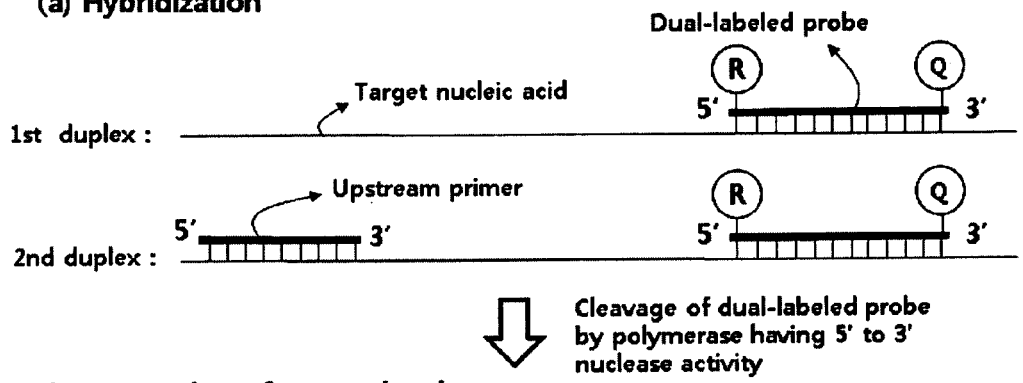

(b) Generation of target signal (i) 5'-3' nuclease activity independent on interaction with primer or extended product of the primer

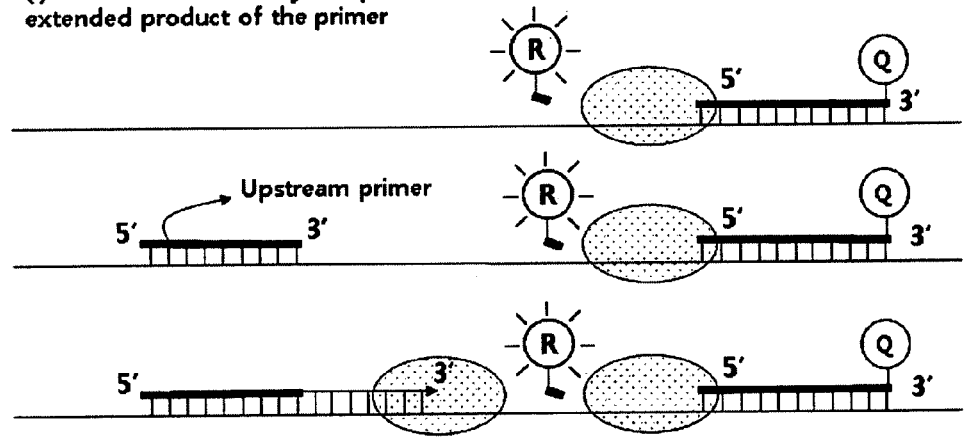

(ii) 5'-3' nuclease activity dependent on interaction with primer or extended product of the primer

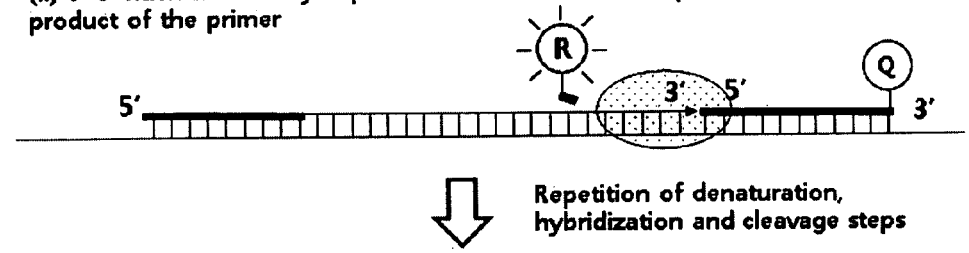

(c) Amplification of target signal

R : Reporter molecule     Q : Quencher molecule

: Nucleic acid polymerase having 5' to 3' nuclease activity

| No. | Template [1] | Dual-labeled probe [2] | Enzyme [3] | Ct value |
|-----|--------------|------------------------|------------|----------|
| 1   | +            | +                      | +          | 1.52     |
| 2   | -            | +                      | +          | -        |
| 3   | +            | +                      | -          | -        |

[1] Template is a synthetic oligonucleotide for *Staphylococcus aureus* gene.
[2] Dual-labeled probe has a reporter molecule and a quencher molecule.
[3] Enzyme is a *Taq* DNA polymerase having 5' to 3' exonuclease activity.

| No. | Template [1] | Dual-labeled probe [2] | Enzyme [3] | Ct value |
|---|---|---|---|---|
| 1 | + | + | + | 2.91 |
| 2 | - | + | + | - |
| 3 | + | + | - | - |

[1] Template is a synthetic oligonucleotide for *Streptococcus pneumoniae* gene.
[2] Dual-labeled probe has a reporter molecule and a quencher molecule.
[3] Enzyme is a *Taq* DNA polymerase having 5' to 3' exonuclease activity.

Fig. 10

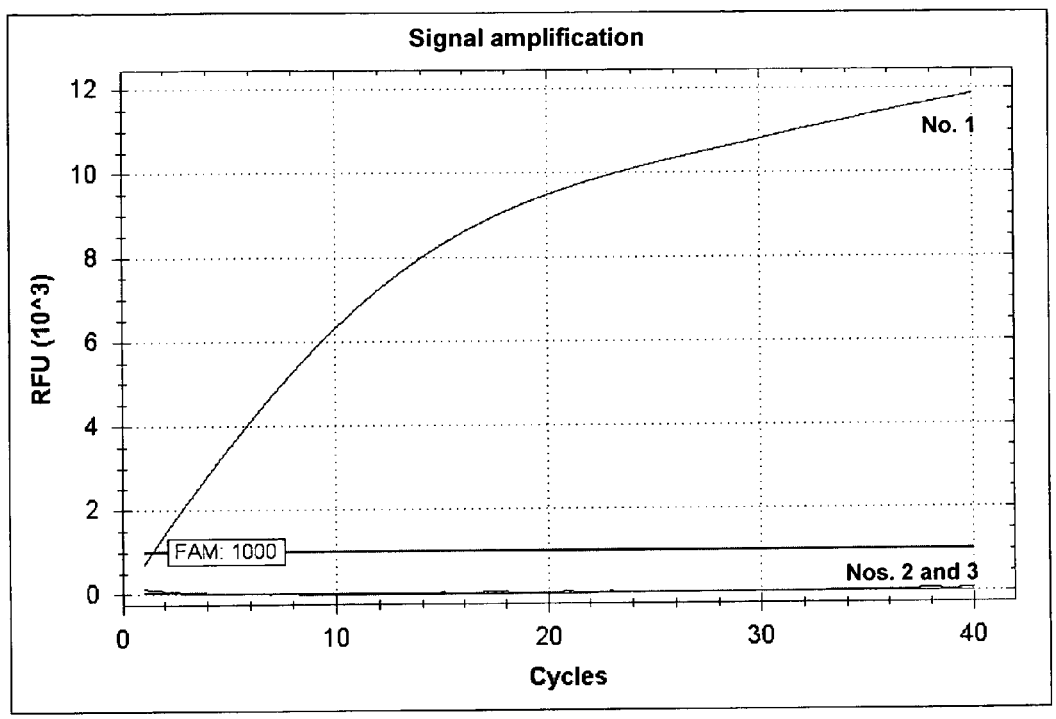

| No. | Template [1] | Mismatch-carrying dual-labeled probe [2] | Enzyme [3] | Ct value |
|---|---|---|---|---|
| 1 | + | + | + | 1.42 |
| 2 | - | + | + | - |
| 3 | + | + | - | - |

[1] Template is a synthetic oligonucleotide for *Neisseria gonorrhoeae* gene.
[2] Mismatch-carrying dual-labeled probe has a reporter molecule and a quencher molecule, and has a mismatch nucleotide at its 3'-end.
[3] Enzyme is a PfuUltra™ II fusion HS DNA polymerase having 3' to 5' exonuclease activity.

| No. | Template [1] | Dual-labeled probe [2] | Enzyme [3] | Ct value |
|---|---|---|---|---|
| 1 | + | + | + | 1.27 |
| 2 | - | + | + | - |

[1] Template is an amplified product of *Streptococcus pneumoniae* genomic DNA.
[2] Dual-labeled probe has a reporter molecule and a quencher molecule.
[3] Enzyme is a *Taq* DNA polymerase having 5' to 3' exonuclease activity.

| No. | Template [1] | Dual-labeled probe [2] | Enzyme [3] | Ct value |
|---|---|---|---|---|
| 1 | + | + | + | 19.73 |
| 2 | - | + | + | - |

[1] Template is a genomic DNA of *Streptococcus pneumoniae*.
[2] Dual-labeled probe has a reporter molecule and a quencher molecule.
[3] Enzyme is a *Taq* DNA polymerase having 5' to 3' exonuclease activity.

DETECTION OF TARGET NUCLEIC ACID SEQUENCES BY CYCLIC EXONUCLEOLYTIC REACTIONS

CROSS-REFERENCE TO RELATED APPLICATIONS

This application is the U.S. national stage filing under 35 U.S.C. §371 of international application PCT/KR2010/002209, filed Apr. 9, 2010, which claims benefit of Korean Patent Application Nos. 10-2009-0090710, filed Sep. 24, 2009 and 10-2009-0103082, filed Oct. 28, 2009.

BACKGROUND OF THE INVENTION

1. Field of the Invention

The present invention relates to the detection of a target nucleic acid sequence by a cyclic exonucleolytic reaction.

2. Description of the Related Art

A target nucleic acid amplification process is prevalently involved in most of technologies for detecting target nucleic acid sequences. Nucleic acid amplification is a pivotal process for a wide variety of methods in molecular biology, such that various amplification methods have been proposed. For example, Miller, H. I. et al. (WO 89/06700) amplified a nucleic acid sequence based on the hybridization of a promoter/primer sequence to a target single-stranded DNA ("ssDNA") followed by transcription of many RNA copies of the sequence. Other known nucleic acid amplification procedures include transcription-based amplification systems (Kwoh, D. et al., *Proc. Natl. Acad. Sci. U.S.A.*, 86:1173 (1989); and Gingeras T. R. et al., WO 88/10315).

The most predominant process for nucleic acid amplification known as polymerase chain reaction (hereinafter referred to as "PCR") is based on repeated cycles of denaturation of double-stranded DNA, followed by oligonucleotide primer annealing to the DNA template, and primer extension by a DNA polymerase (Mullis et al. U.S. Pat. Nos. 4,683,195, 4,683,202, and 4,800,159; Saiki et al., (1985) *Science* 230, 1350-1354).

PCR-based techniques have been widely used not only for amplification of a target DNA sequence, but also for scientific applications or methods in the fields of biological and medical research, such as reverse transcriptase PCR (RT-PCR), differential display PCR (DD-PCR), cloning of known or unknown genes by PCR, rapid amplification of cDNA ends (RACE), arbitrary priming PCR (AP-PCR), multiplex PCR, SNP genome typing, and PCR-based genomic analysis (McPherson and Moller, (2000) PCR. BIOS Scientific Publishers, Springer-Verlag New York Berlin Heidelberg, N.Y.).

In addition, a variety of real-time PCR procedures have been proposed for detecting target nucleic acids. The real-time PCR methods have been highlighted in the senses that they can amplify and detect target sequences in a real-time manner. The real-time PCR procedures generally use labeled-primers or labeled-probes. The illustrative examples of the real-time PCR procedures include TaqMan™ probe method (U.S. Pat. No. 5,210,015), Self-quenching probe method (U.S. Pat. No. 5,723,591), Molecular Beacon method (Tyagi et al, Nature Biotechnology v. 14 Mar. 1996), and Lion method (U.S. Pat. No. 6,248,526).

In TaqMan™ probe method, probes are designed to hybridize to an internal region of a PCR product. While the polymerase replicates a template on which a TaqMan probe is bound, the 5' to 3' exonuclease activity of the polymerase cleaves the probe. This separates the fluorescent and quenching dyes and FRET no longer occurs (Parashar et al, Indian J Med Res 124: 385-398(2006)). According to TaqMan™ probe method, the 5' to 3' exonuclease activity of the polymerase triggers exonucleolytic exoncleolytic reactions only when the polymerase binds to upstream primers or their extended products. When the primer and the probe are designed to be in a proximal position, the 5' to 3' exonuclease activity bound to the primer cleaves the probe close to the primer with no polymerization reactions, called as a polymerization-independent cleavage. Meanwhile, where the primer and the probe are in a distal position, the polymerase extends the primer and its 5' to 3' exonuclease activity bound to the primer extended product cleaves the probe, called as a polymerization-dependent cleavage (U.S. Pat. No. 5,210,015, column 6, line 41 to column 7, line 10).

The Self-quenching probe method or Molecular beacon method uses dual-labeled probes having a sequence hybridizable with an internal region of a PCR product. In both methods, upon hybridization with target sequences, probes generate fluorescent signals by unquenching signals.

The Lion method uses a labeled primer deliberately mismatched in at least one nucleotide at the 3' end of the primer. The labeled primer is incubated with a sample under conditions sufficient to allow hybridization and the sample is subsequently exposed to nucleic acid polymerase having a 3' to 5' proofreading activity, thereby releasing the label or part of the label system.

In light of signal generation, the TaqMan™ probe method has some disadvantages associated with requirement for primers for probe cleavage. For example, the requirement for primers as well as probes becomes a serious obstacle for multiple target detection. The Self-quenching probe method or Molecular beacon method produce no signal accumulation over cycles of PCR reactions, which is considered ineffective in signal generation. In addition, both methods based on hybridization have to detect signals under conditions for hybridization with target sequences. Such signal detection protocol is responsible for their poor applicability to various conditions.

In the meantime, the real-time PCR methods including those described above basically require amplification primers for amplification of target sequences as well as target signals for simultaneous detection of the amplified products. Therefore, they are called homogeneous assays. However, the requirement of amplification primers in the real-time PCR methods provides a limitation in the application for detection of multiple target sequences such as false positive signals and difficulties in oligonucleotides (primer and probe) selection and reaction condition optimization.

Therefore, it could be appreciated that a new approach to amplify signals with no help of simultaneous target amplification may enable to detect multiple target sequences without such problems accounted in the conventional real-time PCR methods.

Throughout this application, various patents and publications are referenced, and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel approaches to detect target sequences in a real-time manner by amplifying efficiently signals for target sequences. As result, we have found that the utilization of probes coupled with exonucleolytic activities results in signal amplification with no help of target amplification reactions to detect target sequences with significant sensitivity and specificity. Also, we have discovered that our novel approaches are successfully adopted to solid phase reactions as well as liquid phase reactions for target detection.

Accordingly, it is an object of this invention to provide a method for detecting a target nucleic acid sequence from a DNA or a mixture of nucleic acids by a cyclic exonucleolytic reaction.

It is another object of this invention to provide a kit for detecting a target nucleic acid sequence from a DNA or a mixture of nucleic acids by a cyclic exonucleolytic reaction.

Other objects and advantages of the present invention will become apparent from the detailed description to follow taken in conjugation with the appended claims and drawings.

BRIEF DESCRIPTION OF THE DRAWINGS

FIG. 1 schematically represents a cyclic exonucleolytic reaction of the present invention in liquid phase. FIG. 1a represents a cyclic exonucleolytic reaction using an enzyme having 5' to 3' exonuclease activity. FIG. 1b represents a cyclic exonucleolytic reaction using an enzyme having 3' to 5' exonuclease activity.

FIG. 2 schematically represents a cyclic exonucleolytic reaction using an enzyme having 5' to 3' exonuclease activity in solid phase. FIG. 2a-(a) represents a step of the pre-amplification of a target nucleic acid. FIG. 2a-(b) represents a step of hybridization between the amplified product and a dual-labeled probe. FIG. 2b-(c) represents a step of cleavage of the dual-labeled probe by the enzyme having 5' to 3' exonuclease activity and signal generation. FIG. 2b-(d) represents a step of target signal amplification by repetition of denaturation, hybridization and cleavage.

FIG. 3 schematically represents a cyclic exonucleolytic reaction using an enzyme having 3' to 5' exonuclease activity in solid phase. FIG. 3a-(a) represents a step of the pre-amplification of a target nucleic acid. FIG. 3a-(b) represents a step of hybridization between the amplified product and a mismatch-carrying dual-labeled probe. FIG. 3b-(c) represents a step of cleavage of the mismatch-carrying dual-labeled probe by the enzyme having 3' to 5' exonuclease activity and signal generation. FIG. 3b-(d) represents a step of target signal amplification by repetition of denaturation, hybridization and cleavage.

FIG. 4 schematically represents a cyclic exonucleolytic reaction using both an enzyme having 5' to 3' exonuclease activity and an enzyme having 3' to 5' exonuclease activity in solid phase. FIG. 4b-(c) represents a target signal amplification by repetition of denaturation, hybridization and cleavage.

FIG. 5 shows three different cases of cleavages of dual-labeled probes independent on interaction with an upstream primer or extended product of the upstream primer.

FIG. 6 shows two different cases of cleavages of dual-labeled probes dependent on interaction with an upstream primer or extended product of the upstream primer.

FIG. 7 schematically represents a cyclic exonucleolytic reaction using a nucleic acid polymerase having 5' to 3' exonuclease activity and an upstream primer. (a) represents a step of hybridization forming first and second duplexs by a target nucleic acid, a dual-labeled probe and the upstream primer. (b) represents a step of cleavage of the dual-labeled probe by two different 5' to 3' exonuclease activities (independent- and dependent-cleavages) and signal generation. (c) represents a step of simultaneous dual-signal amplification by repetition of denaturation, hybridization and cleavage.

FIG. 10 shows the results of a cyclic exonucleolytic reaction using a PfuUltra II DNA polymerase having 3' to 5' exonuclease activity for the detection of *Neisseria gonorrhoeae* gene.

DETAILED DESCRIPTION OF THIS INVENTION

Figure 2B:
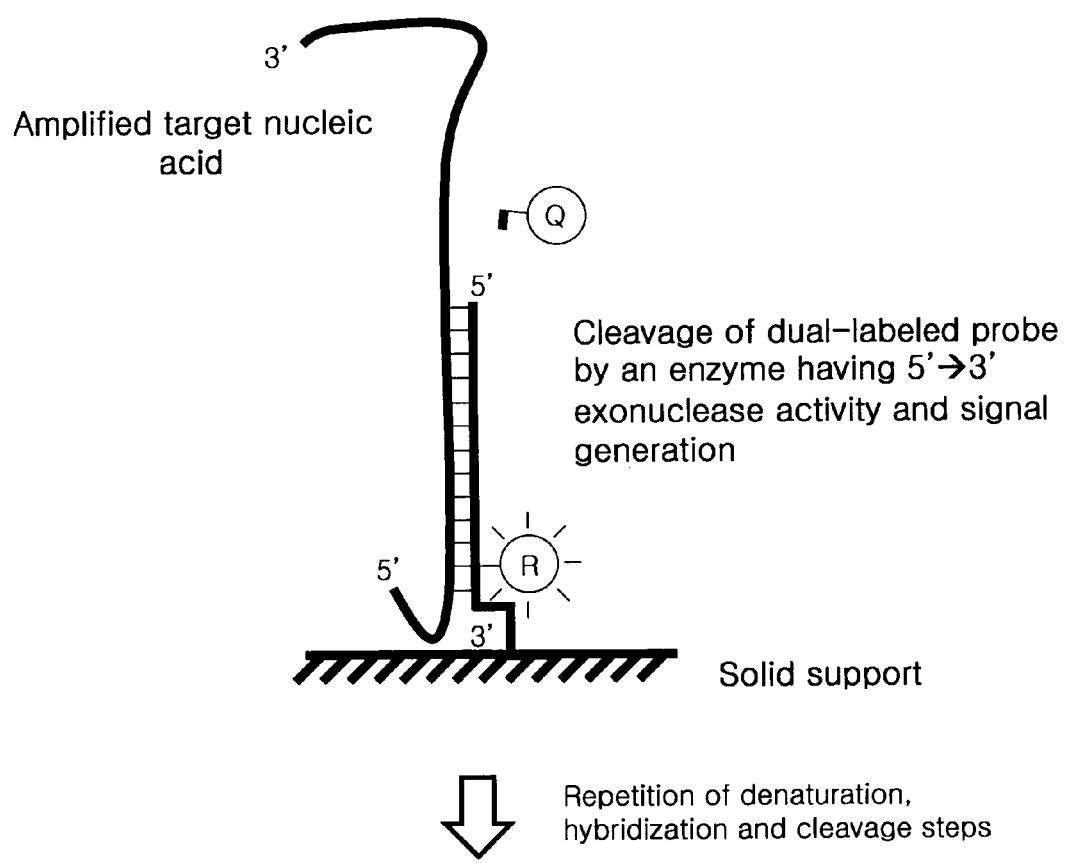
Figure 3B:
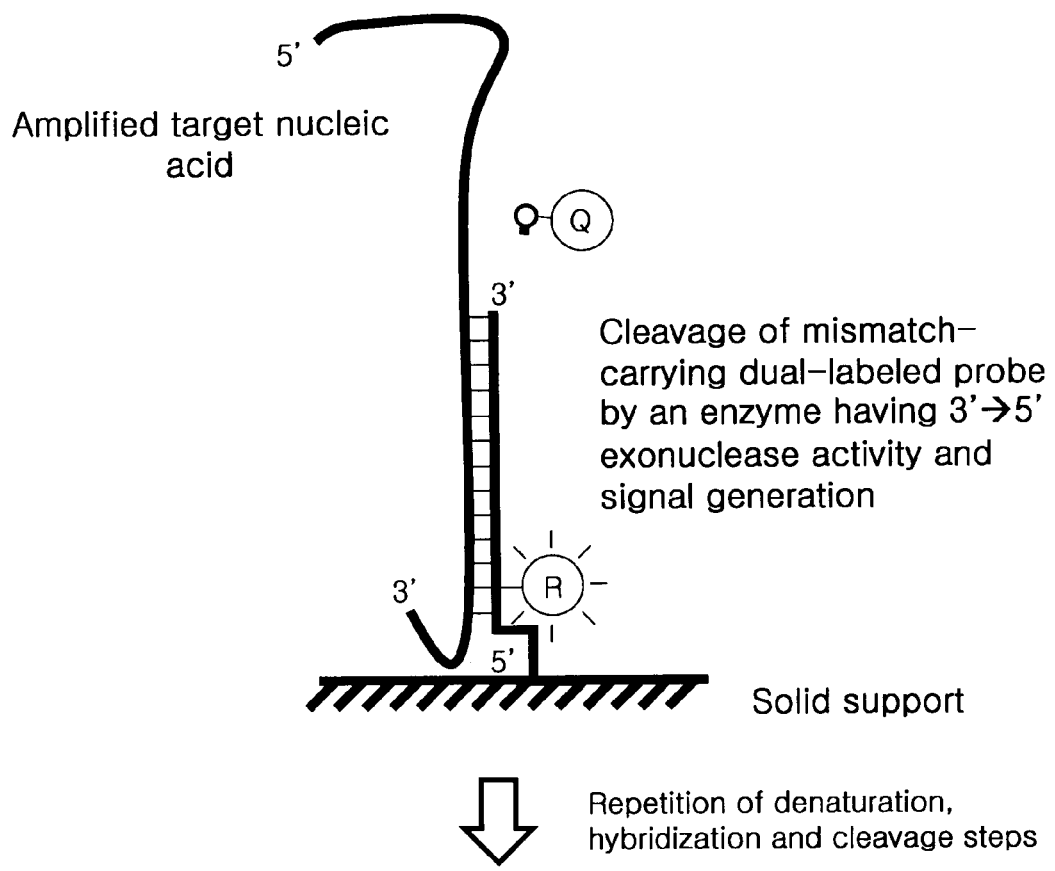
Figure 4A:
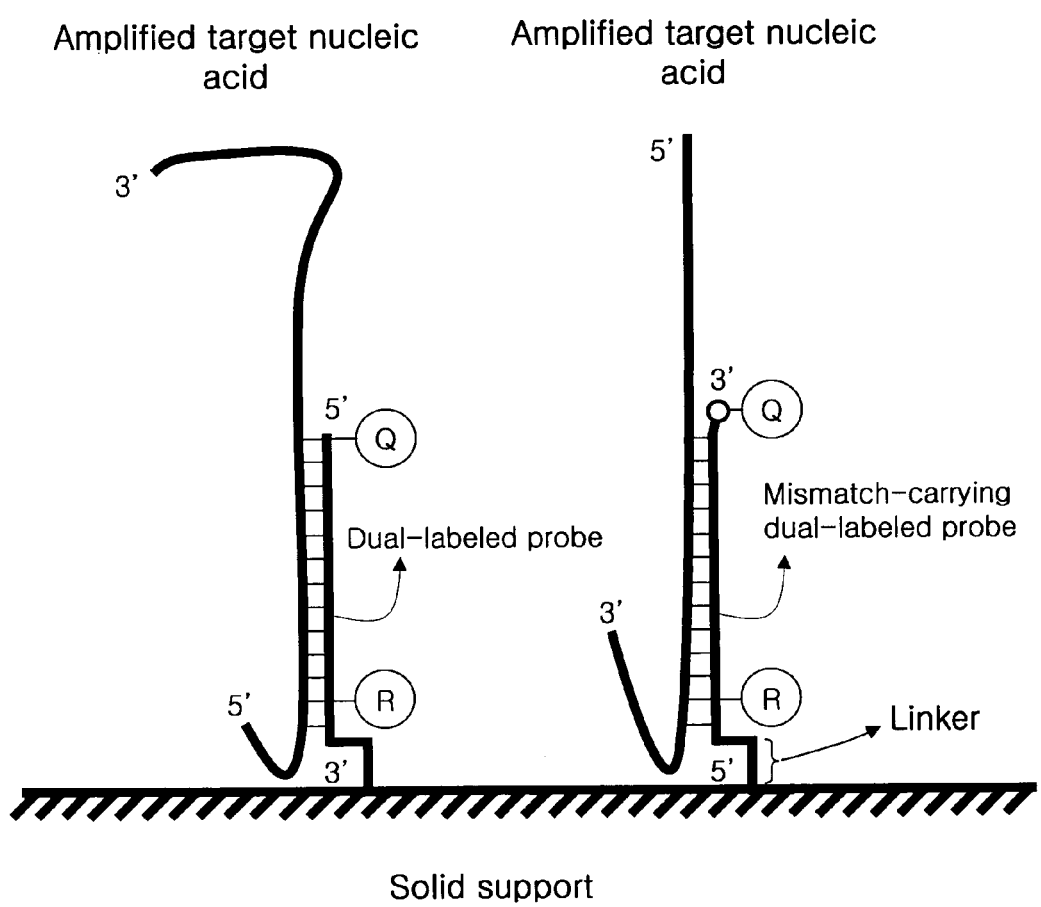
FIG. 4a-(a) represents a hybridization of a dual-labeled probe and a mismatch-carrying dual-labeled probe with an amplified target nucleic acid, respectively.
Figure 4B:
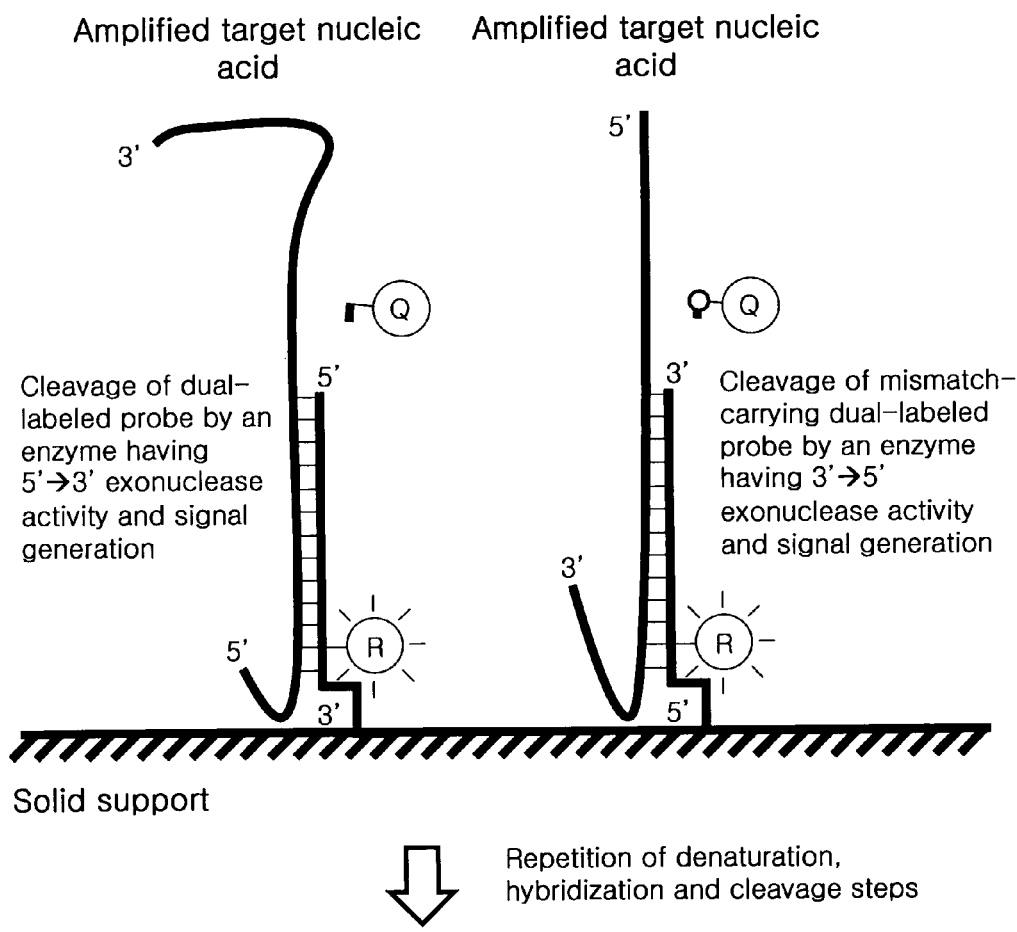
FIG. 4b-(b) represents the cleavage of both the dual-labeled probe and the mismatch-carrying dual-labeled probe by the enzyme having 5' to 3' exonuclease activity and the enzyme having 3' to 5' exonuclease activity, respectively and signal generation.

The present invention is directed to a novel method for a target nucleic acid sequence by cyclic exonucleolytic reactions in a real-time manner.

In one aspect of the present invention, there is provided a method for detecting a target nucleic acid sequence from a DNA or a mixture of nucleic acids by a cyclic exonucleolytic reaction, which comprises the steps of:

(a) hybridizing the target nucleic acid sequence with a probe, wherein the probe has a hybridizing nucleotide sequence complementary to a first site on the target nucleic acid, a fluorescent reporter molecule, and a quencher molecule capable of quenching the fluorescence of the reporter molecule;

(b) contacting the probe to an enzyme having an exonuclease activity for cleavage of the probe, such that either the fluorescent reporter molecule or the quencher molecule is released from the probe to unquench the fluorescence of the reporter molecule and generate a fluorescent signal indicative of the presence of the target nucleic acid sequence;

(c) denaturing a duplex of the probe-target nucleic acid sequence of step (b);

(d) repeating the steps (a)-(c) at least twice to amplify the signal indicative of the presence of the target nucleic acid sequence; and (e) detecting the signal indicative of the presence of the target nucleic acid sequence, wherein the detection is performed for each cycle of the repetition of step (d), at the end of the repetition of step (d) or at each of predetermined time intervals during the repetition, such that the signal is indicative of the presence of the target nucleic acid sequence.

The present inventors have made intensive researches to develop novel approaches to detect target sequences in a real-time manner by efficiently amplifying signals for target sequences. As a result, we have found that the utilization of probes coupled with exonucleolytic activities results in signal amplification with no help of target amplification reactions to detect target sequences with significant sensitivity and specificity. Also, we have discovered that our novel approaches are successfully adopted to solid phase reactions as well as liquid phase reactions for target detection.

In accordance with the present invention, exonucleolytic reactions are repeatedly carried out using probes (dually labeled with a fluorescent reporter molecule and a quencher molecule) and exonucleolytic activities, thereby amplifying fluorescent signals indicative of target sequences even with no help of simultaneous target amplification reactions.

In this regard, the prominent feature of the present invention distinctly different from convention real-time PCR technologies is not to require the amplification of a target nucleic acid sequence for the target signal amplification. The present invention is able to successfully detect a target nucleic acid sequence by (a) utilization of probes dually labeled with a fluorescent reporter molecule and a quencher molecule; (b) signal generation by exonucleolytic reactions catalyzed by an enzyme having exonucleolytic activities, and (c) signal amplification by repetition of hybridization and denaturation with exonucleolytic reactions.

Therefore, the present invention is called "target signal amplification by Cyclic Exonucleolytic Reactions (CER)".

The conventional real-time PCR technologies using dual-labeled oligonucleotides such as TaqMan™ probe method, Self-quenching probe method, Molecular Beacon method, and Lion method involve necessarily amplification reactions of target sequences for signal amplification. In other words, the existing methods increase the number of target sequences in samples to be analyzed by amplifying target sequences using amplification primers, thereby generating more signals indicating target sequences.

In contrast, the present invention permits to amplify signals only by repeating probe hybridization and denaturation with exonucleolytic reactions with no help of target amplification reactions.

The present inventors have verified that 5' to 3' exonucleolytic reactions and/or 3' to 5' exonucleolytic reactions on dual-labeled probes hybridized with target sequences can produce fragments containing a label of the dual label system and that repetition of hybridization and denaturation between dual-labeled probes and target sequences under exonucleolytic reactions results in accumulation of the label-containing fragments (i.e., signal amplification), providing sufficient signal intensities for target detection.

The present invention being able to amplify signals indicating target sequences irrespectively of target amplification does not necessarily demand amplification primers for target detection, which is one of the most prominent advantages of the present invention. Especially, for multiplex detection methods to detect multiple target sequences, conventional real-time PCR methods using oligonucleotides for target amplification as well as oligonucleotides for target detection have shortcomings to be overcome such as false positive signal, difficulty in optimization of oligonucleotide sequences and reaction conditions and cost-ineffectiveness. By contrast, the present invention capable of detecting target sequences only with labeled probes can successfully solve the problems described above.

The CER process of the present invention also has signal-maximizing effects on a solid phase reaction. In brief, when target sequences are hybridized with labeled probes immobilized on a solid substrate, a hybridization extent is determined by reaction conditions. Labeled probes not hybridized with target sequences do not generate signals due to no occurrence of cleavage reactions, which is a main hurdle in conventional hybridization-based chip technologies. Since the present CER method includes repetition of hybridization and denaturation between target sequences and labeled probes, the labeled probes on the solid substrate have much more opportunity to be hybridized with target sequences and to be cleaved by exonucleolytic activities, finally leading to maximization of signal generation.

Furthermore, the present invention to use only signal amplification has advantages over conventionally hybridization-based methods such as Molecular beacon method in which signal generation is dependent only on hybridization rather than probe cleavage reactions.

The inventive concept underlying the present invention in which signals indicating target sequences are generated using dual-labeled probes and exonucleolytic activities and amplified under suitable conditions with no help of simultaneous target amplification reactions to detect target sequences is first proposed by the present inventors.

In the present invention, the target nucleic acid sequence is hybridized with the probe dually labeled with a fluorescent reporter molecule and a quencher molecule.

The term used herein "target nucleic acid", "target nucleic acid sequence" or "target sequence" refers to a nucleic acid sequence of interest for detection, which is annealed to or hybridized with a probe or a primer under hybridization, annealing or amplifying conditions.

The term used herein "probe" refers to a single-stranded nucleic acid molecule comprising a portion or portions that are substantially complementary to a target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", preferably perfectly complementary. Preferably, the probe is a single-stranded deoxyribonucleotide molecule. The probes of this invention may be comprised of naturally occurring dNMP (i.e., dAMP, dGM, dCMP and dTMP), modified nucleotide, or non-natural nucleotide. The probes may also include ribonucleotides. Preferably, the 3'-end of the probe is "blocked" to prohibit the extension of the probe. "Blocking" may be achieved by adding a chemical moiety such as a phosphate group to the 3'-hydroxyl group of the last nucleotide.

The term used "hybridizing" used herein refers to the formation of a double-stranded nucleic acid from complementary single stranded nucleic acids. The hybridization may occur between two nucleic acid strands perfectly matched or substantially matched with some mismatches. The complementarity for hybridization may depend on hybridization conditions, particularly temperature.

There is no intended distinction between the terms "annealing" and "hybridizing", and these terms will be used interchangeably.

The CER method of the present invention may be carried out using an additional primer (forward primer and/or reverse primer). The term used herein "forward primer" means a primer (5' to 3' direction) complementary to a strand of a target nucleic acid sequence aligned in a 3' to 5' direction. According to the present invention, a primer positioned upstream of a probe is called "forward primer" or "upstream primer". The reverse primer has a complementary sequence to the other strand of the nucleic acid sequence.

Where the probe and the reverse primer are used with an enzyme having 5' to 3' exonuclease activity, a template to be hybridized with the probe is selectively increased by nucleic acid synthesis reactions during the repetition step. The increase in the template allows for more rapidly providing signals to detect target sequences. In the meantime, the present invention may be performed using a primer pair (including the forward primer and the reverse primer) as well as the probe to detect target sequences together with target amplification.

Where the CER method is performed using the probe and the upstream primer in the presence of the 5' to 3' exonuclease activity of template-dependent nucleic acid polymerases, the 5' to 3' exonuclease activity activated upon binding to the upstream primer or its extended product digests the probe to generate signals indicative of target sequences.

The CER process of the present invention can be carried out in accordance with the following protocols: (I) liquid phase and solid phase reactions using enzymes having a 5' to 3' exonuclease activity; (II) liquid phase and solid phase reactions using enzymes having a 3' to 5' exonuclease activity; (III) liquid phase and solid phase reactions using enzymes having a 5' to 3' exonuclease activity as well as enzymes having a 3' to 5' exonuclease activity; and (IV) liquid phase and solid phase reactions using enzymes having a 5' to 3' exonuclease activity and upstream primer.

I. CER Process Using Enzymes Having a 5' to 3' Exonuclease Activity

According to our findings, the fluorescent signals indicative of target nucleic acid sequences can be amplified using dual-labeled probes and enzymes having the 5' to 3' exonuclease activity with no use of upstream (forward) primers.

It is considerably interesting and surprising that the 5'-end portion of dual-labeled probes hybridized with target nucleic acid sequences is digested (cleaved) by enzymes having the 5' to 3' exonuclease activity, inter alia, template-dependent nucleic acid polymerases having a 5' to 3' exonuclease activity with no help of primers. Where dual-labeled probes are hybridized with target nucleic acid sequences, their 5'-end portions are digested by the 5' to 3' exonuclease activity of template-dependent nucleic acid polymerases with no occurrence of primer extension reactions. Surprisingly, we have found that the fluorescent signal generated by the 5' to 3' exonuclease activity is generated within one (1) min after contacting to template-dependent nucleic acid polymerases, which are plausibly adopted to the unique signal generation process of the present CER method.

The CER process using enzymes having the 5' to 3' exonuclease activity performed in a liquid phase or a solid phase has been established for target detection on the basis of our discoveries described above.

The TaqMan™ probe method is a representative of technologies to detect target sequences in a real-time manner by probe cleavage reactions with 5' to 3' exonuclease activities of nucleic acid polymerases. According to the TaqMan™ probe method, the 5' to 3' exonuclease activity of a nucleic acid polymerase for probe cleavage is activated only when the nucleic acid polymerase is bound to the primer (located upstream of the probe) or its extended product. Therefore, the upstream primer or its extended product is crucially required in the TaqMan™ probe method for probe cleavage and the binding (or interaction) of the nucleic acid polymerase to the upstream primer or its extended product is also required for probe cleavage (see U.S. Pat. No. 5,210,015). In U.S. Pat. No. 5,210,015, the probe cleavage reaction by the nucleic acid polymerase bound to upstream primers is called a polymerization-independent cleavage and the probe cleavage reaction by the nucleic acid polymerase bound to extended products of upstream primers called a polymerization-independent cleavage. However, U.S. Pat. No. 5,210,015 does not disclose or suggest probe cleavage reactions being independent on primers, which is one of the most crucial implications in the present invention.

Unlike to the TaqMan™ probe method, the 5' to 3' exonuclease activity of nucleic acid polymerases for digestion of probes hybridized with target sequences in an independent manner on primers is combined with dual-labeled probes by strategies of the present invention, generating signals indicative of target sequences.

In the meantime, the TaqMan™ probe method amplifies signals indicative of target sequences by amplifying target sequences. In contrast to this, the present invention not requiring primers amplifies signals indicative of target sequences by repeating hybridization and denaturation, which is extremely unique over conventional real-time PCR technologies including the TaqMan™ probe method.

The technological strategies of the present invention in which the independent 5' to 3' exonuclease activity of nucleic acid polymerases is used to generate signals indicating target sequences and the signals are amplified with no help of simultaneous target amplification are first proposed by the present inventors, which is distinctly different from conventional real-time PCR technologies including the TaqMan™ probe method.

The term used herein "5'-end portion" in conjunction with the probe refers to a portion or region comprising any lengthy consecutive sequence from the 5'-end of the probe. Preferably, the 5'-end portion of the probe is composed of a sequence comprising 1-10 nucleotides (more preferably 1-5 nucleotides, still more preferably 1-3 nucleotides) from its 5'-end.

When using enzymes having the 5' to 3' exonuclease activity, it is preferable that the probe has a match nucleotide sequence at its 5'-end. Most of enzymes having the 5' to 3' exonuclease activity, particularly, template-dependent nucleic acid polymerases having the 5' to 3' exonuclease activity, cleave the 5'-end portion or the 5'-end of only the probe hybridized with the target nucleic acid sequence to form a double strand.

According to the preferred embodiment, the hybridization step is conducted for no more than 2 min, more preferably no more than 1 min 30 sec, still more preferably no more than 1 min. According to the preferred embodiment, the hybridization step is conducted for at least 10 sec, preferably at least 20 sec, more preferably at least 30 sec.

Either a fluorescent reporter molecule or a quencher molecule may be located at any site on the probe, so long as the signal generated from the probe before hybridization differs from that from the probe after cleavage upon hybridization.

Preferably, either the reporter molecule or the quencher molecule on the probe is located at its 5'-end or at 1-5 nucleotides apart from its 5'-end. For example, the reporter molecule on the probe is located at its 5'-end or at 1-5 nucleotides apart from its 5'-end and the quencher molecule is located at 4-50 nucleotides apart from the reporter molecule. Most preferably, either the reporter molecule or the quencher molecule on the probe is located at its 5'-end.

According to a preferred embodiment, the reporter molecule and the quencher molecule are separated by at least 4 nucleotides, more preferably at least 6 nucleotides, still more preferably at least 10 nucleotides, still much more preferably at least 15 nucleotides.

According to a preferred embodiment, the reporter molecule and the quencher molecule are separated by no more than 50 nucleotides, more preferably no more than 30 nucleotides, still more preferably no more than 25 nucleotides, still much more preferably no more than 20 nucleotides.

Where the probe is hybridized with the target nucleic acid sequence, the enzyme having the 5' to 3' exonuclease activity digests its 5'-end portion or its 5'-end and releases either the reporter molecule or the quencher molecule located on its 5'-end portion or its 5'-end, thereby unquenching the fluorescence of the reporter molecule to generate the fluorescent signal indicative of the target nucleic acid sequence.

In a solid phase reaction, the probe is immobilized through its 3'-end on the surface of a solid substrate; wherein the probe has a digested portion and an undigested portion by the 5' to 3' exonuclease activity of the enzyme such that the undigested portion is remained to the surface of the solid substrate; wherein the fluorescent reporter molecule on the probe is positioned on the undigested portion and the quencher molecule capable of quenching the fluorescence of the reporter molecule is positioned on the digested portion; wherein when the probe is hybridized with the target nucleic acid sequence, the digested portion of the probe is released from the probe by the 5' to 3' exonuclease activity of the enzyme and the fluorescence of the report molecule on the undigested portion of the probe is unquenched, whereby a fluorescent signal on the solid substrate is detected to determine the presence of the target nucleic acid sequence.

According to a preferred embodiment, the digested and undigested portions are partitioned by methods for conferring the resistance to the 5' to 3' exonuclease activity such as modified nucleotides or backbones resistant to the 5' to 3' exonuclease activity.

In the solid phase reaction, the quencher molecule is on the digested portion on the probe, preferably the 5'-end of the probe or at 1-5 nucleotides apart from its 5'-end, more preferably the 5'-end. The fluorescent reporter molecule is on the undigested portion on the probe.

According to a preferred embodiment, the reporter molecule and the quencher molecule are separated by at least 4 nucleotides, more preferably at least 6 nucleotides, still more preferably at least 10 nucleotides, still much more preferably at least 15 nucleotides.

As the immobilized probe is continuously digested from its 5'-end by the 5' to 3' exonuclease activity, the binding between a remaining portion of the immobilized probe and the target nucleic acid becomes weaker, thereby resulting in release of the target nucleic acid from the undigested fragment of the immobilized probe on the solid substrate. The release of the target nucleic acid sequence prevents the reporter molecule on the undigested portion of the probe from digesting by the 5' to 3' exonuclease activity. In this regard, the immobilized probe can be considered to have two portions, digested portion and undigested portion by the 5' to 3' exonuclease activity of enzymes (preferably, template-dependent nucleic acid polymerases). Therefore, for generating fluorescent signals indicative of the presence of the target nucleic acid sequence on the solid substrate, the fluorescent reporter molecule preferably is positioned on the undigested portion of the immobilized probe and the quencher molecule capable of quenching the fluorescence of the reporter molecule on the digested portion.

According to a preferred embodiment, when the quencher molecule is fluorescent, the signal indicative of the presence of the target nucleic acid sequence to be detected is a fluorescent signal from the quencher molecule. When the above case is applied particularly to a solid phase reaction, the reporter molecule is on the digested portion on the probe and the quencher molecule is on the undigested portion on the probe.

Preferably, the enzyme having the 5' to 3' exonuclease activity is a thermostable exonuclease, more preferably a template-dependent nucleic acid polymerase having the 5' to 3' exonuclease activity (e.g., *E. coli* DNA polymerase I, a thermostable DNA polymerase and bacteriophage T7 DNA polymerase), most preferably a thermostable DNA polymerase obtained from a variety of bacterial species, including *Thermus aquaticus* (Taq), *Thermus thermophilus*, *Thermus filiformis*, *Thermus flavus*, *Thermus antranikanii*, *Thermus caldophilus*, *Thermus chliarophilus*, *Thermus igniterrae*, *Thermus lacteus*, *Thermus oshimai*, *Thermus ruber*, *Thermus rubens*, *Thermus scotoductus*, *Thermus silvans*, *Thermus species* Z05 and *Thermus* species sps 17. Most preferably, the template-dependent nucleic acid polymerase having the 5' to 3' nuclease activity is Taq DNA polymerase.

In the present CER reactions, it is preferred that the step (a) is performed using an additional reverse primer to produce the target nucleic acid sequence hybridizable with the probe in step (b) by an extension reaction of the additional reverse primer by the template-dependent nucleic acid polymerase.

For the solid phase reaction, the probes may be immobilized directly or indirectly (preferably indirectly) onto the surface of the solid substrate. Furthermore, the probes may be immobilized on the surface of the solid substrate in a covalent or non-covalent manner. Where the immobilized probes are immobilized indirectly onto the surface of the solid substrate, suitable linkers are used. The linkers useful in this invention may include any linkers utilized for probe immobilization on a microarray. For example, alkyl or aryl compounds with amine functionality, or alkyl or aryl compounds with thiol functionality serve as linkers for probe immobilization.

According to a preferred embodiment, the solid substrate used in the present invention is a microarray. The microarray to provide a reaction environment in this invention may include any those known to one of skill in the art. All processes of the present invention, i.e., annealing to target nucleic acid, extension/digestion and fluorescence detection, are carried out on the microarray. The immobilized probes on the microarray serve as hybridizable array elements. The solid substrate to fabricate microarray include, but not limited to, metals (e.g., gold, alloy of gold and copper, aluminum), metal oxide, glass, ceramic, quartz, silicon, semiconductor, $Si/SiO_2$ wafer, germanium, gallium arsenide, carbon, carbon nanotube, polymers (e.g., polystyrene, polyethylene, polypropylene and polyacrylamide), sepharose, agarose and colloids. A plurality of immobilized probes in this invention may be immobilized on an addressable region or two or more addressable regions on a solid substrate that may comprise 2-1,000,000 addressable regions. Immobilized probes may be fabricated to produce array or arrays for a given application by conventional fabrication technologies such as photolithography, ink-jetting, mechanical microspotting, and derivatives thereof.

II. CER Process Using Enzymes Having a 3' to 5' Exonuclease Activity

The present invention may be carried out using an enzyme having 3' to 5' exonucleolytic reactions. Several real-time PCR technologies using the 3' to 5' exonuclease activity for the detection of target sequences were known, including the Lion method disclosed in U.S. Pat. No. 6,248,526. The conventional real-time PCR technologies amplify signals indicative of target sequences by amplifying target sequences as the conventional method using the 5' to 3' exonuclease activity.

Unlikely, the present invention amplifies signals indicating target sequences by repeating hybridization and denaturation. According to the present invention, dNTP is not essential for amplifying signals for target detection.

Where the enzyme having the 3' to 5' exonuclease activity is used, the probe comprises at least one mismatch nucleotide at its 3'-end portion or 3'-end.

The term used herein "3'-end portion" in conjunction with the probe refers to a portion or region comprising any lengthy consecutive sequence from the 3'-end of the probe. Preferably, the 3'-end portion of the probe is composed of a sequence comprising 1-10 nucleotides (more preferably 1-5 nucleotides, still more preferably 1-3 nucleotides) from its 3'-end.

The term used herein "mismatch nucleotide" refers to a non-complementary nucleotide or a nucleotide recognized as mismatched by template-dependent nucleic acid polymerases having a proofreading activity.

The mismatch nucleotide may be located at various sites of the probe. Preferably, the mismatch nucleotide is located at 3'-end portion of the probe.

According to a preferred embodiment, the mismatch nucleotide is present at its 3'-end or 1-5 nucleotides apart from its 3'-end, more preferably at its 3'-end or 1-2 nucleotides apart from its 3'-end, still more preferably at its 3'-end or 1 nucleotide apart from its 3'-end, most preferably, at its 3'-end.

The number of the mismatch nucleotides may be 1-5, preferably 1-4, more preferably 1-3, still more preferably 1-2 and most preferably 1 (single mismatch nucleotide). Where the probe carries at least 2 mismatch nucleotides, the mismatch nucleotides may be located continuously or intermittently.

When an enzyme having the 3' to 5' exonuclease activity is used, either a fluorescent reporter molecule or a quencher molecule may be located on the 3'-end portion of the probe.

Preferably, either the reporter molecule or the quencher molecule is located on the mismatch nucleotide-containing 3'-end portion of the probe. For example, either the reporter molecule or the quencher molecule may be located at the 3'-adjacent site of the mismatch nucleotide on the 3'-end portion of the probe. Alternatively, either the reporter molecule or the quencher molecule may be located at the mismatch nucleotide on the 3'-end portion of the probe.

More preferably, either the reporter molecule or the quencher molecule on the probe is located on the mismatch nucleotide at its 3'-end or at 1-5 nucleotides apart from its 3'-end. Most preferably, either the reporter molecule or the quencher molecule on the probe is located on the mismatch nucleotide at its 3'-end.

According to a preferred embodiment, the reporter molecule and the quencher molecule are separated by at least 4 nucleotides, more preferably at least 6 nucleotides, still more preferably at least 10 nucleotides, still much more preferably at least 15 nucleotides.

According to a preferred embodiment, the reporter molecule and the quencher molecule are separated by no more than 50 nucleotides, more preferably no more than 30 nucleotides, still more preferably no more than 25 nucleotides, still much more preferably no more than 20 nucleotides.

Where the probe is hybridized with the target nucleic acid sequence, the enzyme having the 3' to 5' exonuclease activity digests its 3'-end portion or its 3'-end and releases either the reporter molecule or the quencher molecule located on its 3'-end portion or its 3'-end, thereby unquenching the fluorescence of the reporter molecule to generate the fluorescent signal indicative of the target nucleic acid sequence.

In a solid phase reaction using enzymes having the 3' to 5' exonuclease activity, the probe is immobilized through its 5'-end on the surface of a solid substrate; wherein the probe has a digested portion and an undigested portion by the 3' to 5' exonuclease activity of the enzyme such that the undigested portion is remained to the surface of the solid substrate; wherein the digested portion includes the mismatch nucleotide; wherein the fluorescent reporter molecule on the probe is positioned on the undigested portion and the quencher molecule capable of quenching the fluorescence of the reporter molecule is positioned on the digested portion; wherein when the probe is hybridized with the target nucleic acid sequence, the digested portion of the probe is released from the probe by the 3' to 5' exonuclease activity of the enzyme and the fluorescence of the report molecule on the undigested portion of the probe is unquenched, whereby a fluorescent signal on the solid substrate is detected to determine the presence of the target nucleic acid sequence.

In the solid phase reaction, the quencher molecule is on the digested portion on the probe, preferably the 3'-end of the probe or at 1-5 nucleotides apart from its 3'-end, more preferably the 3'-end. The fluorescent reporter molecule is on the undigested portion on the probe.

Where the liquid or solid phase reaction is carried out using the enzyme having the 3' to 5' exonuclease activity, it is preferable that the probe used has a mismatch-carrying dual specificity oligonucleotide structure represented by the following general formula II:

$$5'\text{-}X_p Y_q\text{-}Z_r\text{-}D_d\text{-}3' \tag{II}$$

wherein, $X_p$ represents a 5'-first hybridization portion having a hybridizing nucleotide sequence complementary to the target nucleic acid sequence, $Y_q$ represents a separation portion comprising at least three universal bases, $Z_r$ represents a 3'-second hybridization portion having a hybridizing nucleotide sequence complementary to the target nucleic acid sequence, and $D_d$ represents a digested portion by the enzyme having the 3' to 5' exonuclease activity and the digested portion has the mismatch nucleotide; the probe is dually labeled with a fluorescent reporter molecule and a quencher molecule capable of quenching the fluorescence of the reporter molecule; the fluorescent reporter molecule or the quencher molecule is positioned on the digested portion; p, q and r represent the number of nucleotides; and X, Y, Z and D are deoxyribonucleotides or ribonucleotides; the $T_m$ of the 5'-first hybridization portion is higher than that of the 3'-second hybridization portion and the separation portion has the lowest $T_m$ in the three portions of $X_p$, $Y_q$ and $Z_r$; the separation portion separates the 5'-first hybridization portion from the 3'-second hybridization portion in terms of hybridization events to the target nucleic acid sequence, whereby the hybridization specificity of the probe are determined dually by the 5'-first hybridization portion and the 3'-second hybridization portion such that the overall hybridization specificity of the probe is enhanced.

The mismatch-carrying DSO (dual specificity oligonucleotide) may be described with reference to descriptions for the DPO described below.

Preferably, the 5'-first hybridization portion is longer than the 3'-second hybridization portion. The 5'-first hybridization portion is preferably 15-60 nucleotides, more preferably 15-40 nucleotides, still more preferably 15-25 nucleotides in length. It is preferable that the 3'-second hybridization portion is 3-15 nucleotides, more preferably 5-15 nucleotides, still more preferably 6-13 nucleotides in length. The separation portion is preferably 3-10 nucleotides, more preferably 4-8 nucleotides, most preferably 5-7 nucleotides in length.

According to a preferred embodiment, the $T_m$ of the 5'-first hybridization portion ranges from 40° C. to 80° C., more preferably 45° C. to 65° C. The $T_m$ of the 3'-second hybridization portion ranges preferably from 10° C. to 40° C. It is preferable that the Tm of the separation portion ranges from 3° C. to 15° C.

According to a preferred embodiment, the enzyme having the 3' to 5' exonuclease activity is a thermostable exonuclease, more preferably a template-dependent nucleic acid polymerase having the 3' to 5' exonuclease activity.

More preferably, the template-dependent nucleic acid polymerase having the 3' to 5' exonuclease activity is a thermostable DNA polymerase obtained from a variety of bacterial species, including *Thermococcus litoralis*, *Thermococcus barossi*, *Thermococcus gorgonarius*, *Thermotoga maritima*, *Thermotoga neapolitana*, *Thermosipho africanus*, *Pyrococcus furiosus* (Pfu), *Pyrococcus woesei*, *Pyrococcus horikoshii*, *Pyrococcus abyssi*, *Pyrodictium occultum*, *Aquifex pyrophilus* and *Aquifex aeolieus*. Most preferably, the template-dependent nucleic acid polymerase having the 3' to 5' nuclease activity is Pfu DNA polymerase.

III. CER Process Using Both Enzymes Having a 5' to 3' Exonuclease Activity and Enzymes Having a 3' to 5' Exonuclease Activity Furthermore, the present invention may be performed using both enzymes having a 5' to 3' exonuclease activity and enzymes having a 3' to 5' exonuclease activity. For this process, both the probe suitable for 5' to 3' exonuclease activity and the probe for 3' to 5' exonuclease activity described above are simultaneously used.

The present invention is drawn to a method for detecting a target nucleic acid sequence from a DNA or a mixture of nucleic acids by a cyclic exonucleolytic reaction, which comprises the steps of:

(a) hybridizing the target nucleic acid sequence with (i) a first probe and (ii) a second probe, wherein the first probe has a hybridizing nucleotide sequence complementary to a first site on the target nucleic acid, a fluorescent reporter molecule, and a quencher molecule capable of quenching the fluorescence of the reporter molecule, wherein the second probe has a hybridizing nucleotide sequence complementary to a second site on the target nucleic acid, an artificial mismatch nucleotide sequence on its 3'-end portion, a fluorescent reporter molecule, and a quencher molecule capable of quenching the fluorescence of the reporter molecule;

(b) contacting the first probe and the second probe to both an enzyme having a 5' to 3' exonuclease activity and an enzyme having a 3' to 5' exonuclease activity, wherein the first probe is cleaved by the enzyme having the 5' to 3' exonuclease activity and the second probe is cleaved by the enzyme having the 3' to 5' exonuclease activity, wherein the fluorescent reporter molecule or the quencher molecule is released from the first probe and the second probe to unquench the fluorescence of the reporter molecule and generate a fluorescent signal indicative of the presence of the target nucleic acid sequence;

(c) denaturing duplexes of the probe-target nucleic acid sequence of step (b);

(d) repeating the steps (a)-(c) at least twice to amplify the signal indicative of the presence of the target nucleic acid sequence; and (e) detecting the signal indicative of the presence of the target nucleic acid sequence, wherein the detection is performed for each cycle of the repetition of step (d), at the end of the repetition of step (d) or at each of predetermined time intervals during the repetition, such that the signal is indicative of the presence of the target nucleic acid sequence.

This process is called "Two Orientation Cyclic Exonucleolytic Reactions (TO-CER)" in the senses that two exonucleolytic enzymes used have different directions from each other.

In the TO-CER reaction, the probe cleaved by the enzyme having the 5' to 3' exonuclease activity or the enzyme having the 3' to 5' exonuclease activity is designed as described in the protocol I or II, respectively.

Furthermore, the probe for the enzyme having the 3' to 5' exonuclease activity is preferably designed not to be cleaved by the 5' to 3' exonuclease activity as follows: (i) use of a blocker resistant to the 5' to 3' exonuclease activity, (ii) proximal location of the reporter molecule and the quencher molecule, or (iii) use of non-complementary sequence on the 5'-end portion of the probe.

Preferably, the probe rendered not to be cleaved by the 5' to 3' exonuclease activity is prepared to contain a blocker with a backbone resistant to the 5' to 3' exonuclease activity. The backbone resistant to the 5' to 3' exonuclease activity includes any one known to one of skill in the art. For example, it includes various phosphorothioate linkages, phosphonate linkages, phosphoroamidate linkages and 2'-carbohydrates modifications. According to a more preferred embodiment, nucleotides having a backbone resistant to the 5' to 3' exonuclease include phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-β-D-ribofuranosyl) modification. The blocker nucleotide present in the probes may be one or more in continuous or intermittent manner.

Alternatively, the probe is rendered not to be cleaved by the 5' to 3' exonuclease activity by locating proximally the reporter molecule and the quencher molecule on its 3'-end portion. Even though the probe is digested by the 5' to 3' exonuclease activity, the reporter molecule and the quencher molecule in a close distance are not separated from each other, not generating signals. For example, where the reporter molecule is linked to a mismatch nucleotide at the 3'-end of the probe and the quencher molecule to a nucleotide at 3 nucleotides apart from the 3'-end, a sequence spanning the mismatch nucleotide and the quencher-linked nucleotide on the probe is not bound to target sequences at certain hybridization to temperatures and its 3'-adjacent site is subject to cleavage by the 5' to 3' exonuclease activity.

Therefore, the reporter molecule and the quencher molecule in a close distance are not separated from each other, not generating false signals by the 5' to 3' exonuclease activity.

In addition, another approach is to use a non-complementary sequence on the 5'-end portion of the mismatch-carrying probe. While the mismatch-carrying probe is hybridized with the target nucleic acid sequence, its 5'-end portion forms a single strand not to be cleaved by the 5' to 3' exonuclease activity.

A solid phase reaction of the TO-CER reaction can be described with reference to descriptions of CER reactions indicated hereinabove.

IV. CER Process Using a Polymerase Having a 5' to 3' Exonuclease Activity and an Upstream Primer Our CER reactions can be carried out using an upstream primer as well as a probe.

In the CER process using the 5' to 3' exonuclease activity of a polymerase, the upstream primer and the probe, two different exonuclease activities are employed: (i) a 5' to 3' exonuclease activity being independent on interaction with either the upstream primer or an extended product of the upstream primer; and (ii) a 5' to 3' exonuclease activity being dependent on interaction with either the upstream primer or an extended product of the upstream primer.

We have newly constructed the CER-UP (Cyclic Exonucleolytic Reaction with Upstream Primer) process using the two different 5' to 3' exonuclease activities, such that the signal indicative of the target nucleic acid sequence is dually generated to detect the target nucleic acid sequence in a more efficient fashion.

According to the present invention, a primer positioned upstream of a probe is called "upstream primer" or "forward primer".

According to a preferred embodiment, the step (a) further comprises an upstream primer having a hybridizing nucleotide sequence complementary to a second site on the target nucleic acid and the 3'-end of the primer is present upstream of the 5'-end of the probe. According to a preferred embodiment, the step (a) is performed by hybridizing the target nucleic acid sequence with both the probe and the primer to form a first duplex by the target nucleic acid sequence and the probe and a second duplex by the target nucleic acid sequence, the probe and the primer.

According to a preferred embodiment, the step (b) is performed by contacting the resultant of step (a) to the template-dependent nucleic acid polymerase having the 5' to 3' exonuclease activity; wherein when the probe is hybridized with the target nucleic acid sequence, the probe is cleaved by (i) the 5' to 3' exonuclease activity of the template-dependent nucleic acid polymerase that is independent on interaction with either the primer or an extended product of the primer, such that either the fluorescent reporter molecule or the quencher molecule is released from the probe to unquench the fluorescence of the reporter molecule and generate a first fluorescent signal, and (ii) the 5' to 3' exonuclease activity of the template-dependent nucleic acid polymerase that is dependent on interaction with either the primer or the extended product of the primer, such that either the fluorescent reporter molecule or the quencher molecule is released from the probe to unquench the fluorescence of the reporter molecule and generate a second fluorescent signal, whereby the fluorescent signals are dually generated in a simultaneous manner.

According to a preferred embodiment, the step (d) is performed by repeating the steps (a)-(c) at least twice to amplify the first fluorescent signal and the second fluorescent signal, thereby resulting in a simultaneous dual-signal amplification.

Preferably, the CER-UP process for detecting a target nucleic acid sequence from a DNA or a mixture of nucleic acids by a cyclic exonucleolytic reaction comprises the steps of:

(a) hybridizing the target nucleic acid sequence with a probe and a primer as a upstream primer to form a first duplex by the target nucleic acid sequence and the probe and a second duplex by the target nucleic acid sequence, the probe and the primer, wherein the probe has a hybridizing nucleotide sequence complementary to a first site on the target nucleic acid, a fluorescent reporter molecule, and a quencher molecule capable of quenching the fluorescence of the reporter molecule; the primer has a hybridizing nucleotide sequence complementary to a second site on the target nucleic acid and the 3'-end of the primer is present upstream of the 5'-end of the probe (b) contacting the first duplex and the second duplex to a template-dependent nucleic acid polymerase having a 5' to 3' exonuclease activity; wherein when the probe is hybridized with the target nucleic acid sequence, the probe is cleaved by (i) the 5' to 3' exonuclease activity of the template-dependent nucleic acid polymerase that is independent on interaction with either the primer or an extended product of the primer, such that either the fluorescent reporter molecule or the quencher molecule is released from the probe to unquench the fluorescence of the reporter molecule and generate a first fluorescent signal, and (ii) the 5' to 3' exonuclease activity of the template-dependent nucleic acid polymerase that is dependent on interaction with either the primer or the extended product of the primer, such that either the fluorescent reporter molecule or the quencher molecule is released from the probe to unquench the fluorescence of the reporter molecule and generate a second fluorescent signal, whereby the fluorescent signals are dually generated in a simultaneous manner;

(c) denaturing the first duplex and the second duplex of step (b);

(d) repeating the steps (a)-(c) at least twice to amplify the first fluorescent signal and the second fluorescent signal indicative of the presence of the target nucleic acid sequence, resulting in a dual simultaneous signal amplification; and (e) detecting the signals indicative of the presence of the target nucleic acid sequence, wherein the detection is performed for each cycle of the repetition of step (d), at the end of the repetition of step (d) or at each of predetermined time intervals during the repetition, such that the signals are indicative of the presence of the target nucleic acid sequence.

The term "5' to 3' exonuclease activity being independent on interaction with either the primer or an extended product of the primer" (hereinafter referred to as independent 5' to 3' exonuclease activity) means exonucleolytic activities being capable of catalyzing 5' to 3' exonucleolytic reactions by acting on probes hybridized with target sequences even (i) in the absence of upstream primers or extended products of upstream primers, or (ii) under conditions that upstream primers or extended products of upstream primers and template-dependent nucleic acid polymerases having the 5' to 3' exonuclease activity bound to probes are not close to each other sufficiently to interact with them.

The term "5' to 3' exonuclease activity being dependent on interaction with either the primer or an extended product of the primer" (hereinafter referred to as dependent 5' to 3' exonuclease activity) means 5' to 3' exonucleolytic activities of template-dependent nucleic acid polymerases bound to upstream primers or extended products of upstream primers acting on probes hybridized with target sequences.

The simultaneous employment of the independent 5' to 3' exonuclease activity and the dependent 5' to 3' exonuclease activity is first suggested by the present invention.

By the independent and dependent 5' to 3' exonuclease activities, the probe is digested in two different patterns to dually generate signals indicative of the target nucleic acid sequence.

The term used herein "dual signal amplification" refers to that signals indicative of the target nucleic acid sequence (a first fluorescent signal and a second fluorescent signal) are dually generated by digesting the probe hybridized with the target nucleic acid sequence in two different cleavage patterns with the independent and dependent 5' to 3' exonuclease activities and are amplified by repeating steps (a)-(c).

The term used herein "dual simultaneous signal amplification" refers to that the dual signal amplification occurs simultaneously. As shown in FIG. 7, the probe is digested by the independent and dependent 5' to 3' exonuclease activities in a simultaneous manner, thereby leading to occurrence of the dual simultaneous signal amplification. In this context, the CER-UP is also named "Real Time-Dual Simultaneous Signal Amplification (Real Time-DSSA)".

The CER-UP process can be described with reference to description of the CER process discussed hereinabove. For example, the probe, the target nucleic acid sequence and hybridization for the CER-UP process can be described with referring to those for the CER process indicated above.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. The primer is preferably single stranded for maximum efficiency in amplification. Preferably, the primer is an oligodeoxyribonucleotide. The primer of this invention may be comprised of naturally occurring dNMP (i.e., dAMP, dGM, dCMP and dTMP), modified nucleotide, or non-natural nucleotide. The primer may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The upstream primer has a hybridizing nucleotide sequence complementary to a second site on the target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", preferably perfectly complementary.

The probe has a hybridizing nucleotide sequence complementary to a first site on the target nucleic acid sequence. The probe has no sequence designated by the upstream primer. In this context, the target nucleic acid sequence may be probed by the upstream primer as well as the probe.

Where the probe and the upstream primer are hybridized with the target nucleic acid sequence, the 3'-end of the upstream primer must be present upstream of the 5'-end of the probe.

By the hybridization, the first duplex by the target nucleic acid sequence and the probe and the second duplex by the target nucleic acid sequence, the probe and the upstream primer are formed. The probes in the first duplex and the second duplex are digested by the 5' to 3' exonuclease activity of the template-dependent nucleic acid polymerase under conditions for primer extension of the upstream primer.

The digestion or cleavage of the probe occurs in accordance with the two different patters to generate signals: (i) a first fluorescent signal from cleavage reactions by the 5' to 3' exonuclease activity being independent on interaction with either the upstream primer or an extended product of the upstream primer; and (ii) a second fluorescent signal from cleavage reactions by the 5' to 3' exonuclease activity being dependent on interaction with either the upstream primer or an extended product of the upstream primer.

More detail, the cleavage reactions by the independent 5' to 3' exonuclease activity causing the first fluorescent signal occur in three different fashions.

The first fashion is that the independent 5' to 3' exonuclease activity acts on the first duplex by the probe and the target nucleic acid sequence to digest the probe, generating the first fluorescent signal.

The second is that the independent 5' to 3' exonuclease activity acts on the probe in the second duplex without interaction with the upstream primer to digest the probe, generating the first fluorescent signal.

The third is that the independent 5' to 3' exonuclease activity acts on the probe in the second duplex without interaction with the extended product of the upstream primer to digest the probe, generating the first fluorescent signal.

In summary, the cleavage reaction by the 5' to 3' exonuclease activity of the template-dependent nucleic acid polymerase being independent on interaction with either the upstream primer or an extended product of the upstream primer occurs at (i) the first duplex by the target nucleic acid sequence and the probe, (ii) the second duplex by the target nucleic acid sequence, the probe and the upstream primer wherein the upstream primer is not extended and the 3'-end of the upstream primer is apart from the 5'-end of the probe to an extent that the probe is not cleaved by the 5' to 3' exonuclease activity being dependent on interaction with the upstream primer, or (iii) the second duplex by the target nucleic acid sequence, the probe and the upstream primer wherein the upstream primer is extended by the template-dependent nucleic acid polymerase and the 3'-end of the extended upstream primer is apart from the 5'-end of the probe to an extent that the probe is not cleaved by the 5' to 3' exonuclease activity being dependent on interaction with the extended product of the upstream primer.

It is very crucial for the detection accuracy of target sequences that the first fluorescent signal by the 5' to 3' exonuclease activity of the template-dependent nucleic acid polymerase being independent on interaction with either the upstream primer or an extended product of the upstream primer is generated. For example, approaches to remove false signals in conventional real-time technologies are all focused on the 5' to 3' exonuclease activity dependent on the upstream primer or extended product. However, false signals can be elicited in the first fluorescent signal in accordance with the present invention but such false signals were not considered in conventional real-time technologies. In this regard, the conventional real-time technologies are likely to possess inherent false data. Therefore, reaction optimization for removal of false signals in generation of the first fluorescent signal should be done. The reactions according to the present invention may be optimized in considering generation of the first fluorescent signal.

The cleavage reactions by the dependent 5' to 3' exonuclease activity causing the second fluorescent signal may occur in accordance with cleavage reactions of conventional real-time PCR processes.

In the present invention, where the target nucleic acid sequence is hybridized with the probe and the upstream primer and the upstream primer is apart from the probe to an extent that the upstream primer is not interacted with the probe, the probe is cleaved by the 5' to 3' exonuclease activity being independent on interaction with the extended product of the upstream primer. According to a preferred embodiment, the 5'-end of the probe in the second duplex is apart by at least 25 nucleotides (more preferably, 25-100 nucleotides, still more preferably 25-50 nucleotides) from the 3'-end of the upstream primer.

According to a preferred embodiment, the CER-UP is performed using an additional reverse primer to amplify the target nucleic acid sequence by a PCR reaction (polymerase chain reaction).

Preferably, the template-dependent nucleic acid polymerase having the 5' to 3' exonuclease activity is a thermostable exonuclease, more preferably a template-dependent nucleic acid polymerase having the 5' to 3' exonuclease activity (e.g., *E. coli* DNA polymerase I, a thermostable DNA polymerase and bacteriophage T7 DNA polymerase), most preferably a thermostable DNA polymerase obtained from a variety of bacterial species, including *Thermus aquaticus* (Taq), *Thermus thermophilus, Thermus filiformis, Thermus flavus, Thermus antranikianii, Thermus caldophilus, Thermus chliarophilus, Thermus igniterrae, Thermus lacteus, Thermus oshimai, Thermus ruber, Thermus rubens, Thermus scotoductus, Thermus silvanus, Thermus species Z05* and *Thermus* species sps 17. Most preferably, the template-dependent nucleic acid polymerase having the 5' to 3' nuclease activity is Taq DNA polymerase.

The CER-UP process may be also carried in not only a liquid phase reaction but also a solid phase reaction as the CER process using enzymes having the 5' to 3' exonuclease activity described in Protocol I. The liquid phase and solid phase reactions in accordance with the CER-UP process may be described with referring to descriptions for the CER process using enzymes having the 5' to 3' exonuclease activity described in Protocol I, except that the upstream primer is used and two different 5' to 3' exonuclease activity of a polymerase are used in the CER-UP process.

In the present CER reactions including CER-UP, the labels on probes are an interactive label system, still more preferably FRET label system. The interactive label system is a signal generating system in which energy is passed non-radioactively between a donor molecule (reporter molecule) and an acceptor molecule (quencher molecule).

As a representative of the interactive label system, the FRET (fluorescence resonance energy transfer) label system includes a reporter molecule (donor molecule) and a quencher molecule (acceptor molecule). In FRET, the energy donor is fluorescent, but the energy acceptor may be fluorescent or non-fluorescent.

In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent.

More preferably, the signal indicative of the target nucleic acid sequence is generated by interactive label systems, most preferably the FRET label system.

In the present CER reactions including CER-UP, the reporter molecule and the quencher molecule useful in the probe may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), 5-FAM (522), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), Dil (565), BODIPY TMR (568), BODIPY558/568 (568), BODIPY564/570 (570), Cy3™ (570), Alexa™ 5464 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC (5) (665), Cy5™ (670), Thiadicarbocyanine (671) and Cy5.5 (694). The numeric in parenthesis is a maximum emission wavelength in nanometer.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition, Molecular Probes, Eugene, Oreg., 1996; U.S. Pat. Nos. 3,996,345 and 4,351,760.

It is noteworthy that a non-fluorescent black quencher molecule capable of quenching a fluorescence of a wide range of wavelengths or a specific wavelength may be used in the present invention.

In the label system adopted to the probe, the reporter encompasses a donor of FRET and the quencher encompasses the other partner (acceptor) of FRET. For example, a fluorescein dye is used as the reporter and a rhodamine dye as the quencher.

Following the hybridization and signal generation, the denaturation of duplexes is carried out. Methods for denaturation includes, but not limited to, heating, alkali, formamide, urea and glycoxal treatment, enzymatic methods (e.g., helicase action) and binding proteins. For instance, the denaturation may be achieved by heating at temperature ranging from 80° C. to 105° C. General methods for accomplishing this treatment are provided by Joseph Sambrook, et al., Molecular Cloning, A Laboratory Manual, Cold Spring Harbor Laboratory Press, Cold Spring Harbor, N.Y. (2001).

The steps (a)-(c) are repeated to amplify signals from the reporter molecule indicative of the target nucleic acid sequence. The number of the cycle repetition is not particularly limited, typically at least two, preferably at least five, more preferably at least ten.

Finally, the signal indicative of the presence of the target nucleic acid sequence is detected. The signal detection may be performed for each cycle of the repetition (i.e., real-time manner), at the end of the repetition (i.e., end-point manner) or at each of predetermined time intervals during the repetition. Preferably, the signal detection may be performed for each cycle of the repetition to improve the detection accuracy.

The signal may be detected or measured by conventional methods for each label. For example, the fluorescence signal may be detected or measured by conventional methods, e.g., fluorometers.

The present invention does not require any particular sequence or length of the target nucleic acid sequences to be detected and/or amplified.

Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Acids Res. 16:10366 (1988)). For reverse transcription, a random hexamer or an oligonucleotide dT primer hybridizable to mRNA can be used.

The oligonucleotide dT primer is comprised of dTMPs, one or more of which may be replaced with other dNMPs so long as the dT primer can serve as primer. Reverse transcription can be done with reverse transcriptase that has RNase H activity. If one uses an enzyme having RNase H activity, it may be possible to omit a separate RNase H digestion step by carefully choosing the reaction conditions.

In particular, target nucleic acid sequences which may be detected and/or amplified include any naturally occurring procaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

The advantages of the present invention may be highlighted in the simultaneous (multiplex) detection of at least two target nucleic acid sequences.

According to a preferred embodiment, the target nucleic acid sequence comprises at least two types (more preferably, at least three types, still more preferably at least five types) of nucleic acid sequences and the probe (and/or upstream primer) comprises at least two types (more preferably, at least three types, still more preferably at least five types) of probes.

For example, where the present invention is performed using a reaction vessel containing five probes (each having a fluorescent reporter molecule with different emission wavelength) and a nucleic acid sample, it generates five different fluorescence signals corresponding to five different target nucleic acids, permitting the simultaneous detection of the five different target nucleic acid sequences in a real-time manner. In this case, all of quencher molecules used may be selected to have different properties from each other. Alternatively, all or some of quencher molecules used may be selected to have the same properties.

Furthermore, the present invention is very useful in detection of a nucleotide variation. The term "nucleotide variation" used herein refers to a nucleotide polymorphism in a DNA sequence at a particular location among contiguous DNA segments that are otherwise similar in sequence. Such contiguous DNA segments include a gene or any other portion of a chromosome. For example, the nucleotide variation detected in the present invention includes SNP (single nucleotide polymorphism), deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations.

According to a preferred embodiment, the target nucleic acid sequence used in the present invention is a pre-amplified nucleic acid sequence obtained using an amplification primer. The utilization of the pre-amplified nucleic acid sequence permits to significantly increase the sensitivity and specificity of target detection of the present invention. The target nucleotide sequence in a smaller amount is pre-amplified to give a suitable amount and then detected by the present method, elevating the sensitivity and specificity of target detection of the present invention.

According to a preferred embodiment, the upstream and/or reverse primer additionally used for the present CER reaction including the CER-UP and/or the amplification primer for pre-amplification of target nucleic acid sequence have a dual priming oligonucleotide (DPO) structure represented by the following general formula I:

$$5'\text{-}X_p\text{-}Y_q\text{-}Z_r\text{-}3' \tag{I}$$

wherein, $X_p$ represents a 5'-first priming portion having a hybridizing nucleotide sequence complementary to the target nucleic acid; $Y_q$ represents a separation portion comprising at least three universal bases, $Z_r$ represents a 3'-second priming portion having a hybridizing nucleotide sequence complementary to the target nucleic acid; p, q and r represent the number of nucleotides, and X, Y, and Z are deoxyribonucleotides or ribonucleotides; the Tm of the 5'-first priming portion is higher than that of the 3'-second priming portion and the separation portion has the lowest Tm in the three portions; the separation portion separates the 5'-first priming portion from the 3'-second priming portion in terms of annealing events to the target nucleic acid, whereby the annealing specificity of the oligonucleotide are determined dually by the 5'-first priming portion and the 3'-second priming portion such that the overall annealing specificity of the primer is enhanced.

The DPO structure as a primer version of DSO (dual specificity oligonucleotide) was first proposed by the present inventor (see WO 2006/095981; Chun et al., Dual priming oligonucleotide system for the multiplex detection of respiratory viruses and SNP genotyping of CYP2C19 gene, *Nucleic Acid Research,* 35:6e40(2007)).

The DPO embodies a novel concept in which its hybridization or annealing is dually determined by the 5'-high $T_m$ specificity portion (or the 5'-first priming portion) and the 3'-low $T_m$ specificity portion (or the 3'-second priming portion) separated by the separation portion, exhibiting dramatically enhanced hybridization specificity (see WO 2006/095981; Kim et al., Direct detection of lamivudine-resistant hepatitis B virus mutants by multiplex PCR using dual-priming oligonucleotide primers, *Journal of Virological Methods,* 149:76-84(2008); Kim, et. al., Rapid detection and identification of 12 respiratory viruses using a dual priming oligonucleotide system-based multiplex PCR assay, Journal of Virological Methods, doi:10.1016/j.jviromet.2008.11.007(2008); Horii et. al., Use of dual priming oligonucleotide system to detect multiplex sexually transmitted pathogens in clinical specimens, Letters in Applied Microbiology, doi:10.111/j.1472-765X2009.02618x(2009)). As such, the DPO has eventually two primer segments with distinct hybridization properties: the 5'-first priming portion that initiates stable hybridization, and the 3'-second priming portion that mainly determines target specificity.

The amplification (particularly, multiplex amplification) using primers having the DPO structure in the present invention ensures to obtain amplicons without false positive and negative data.

According to a preferred embodiment, the universal base in the separation portion is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'O-methoxyethyl nebularine, 2'-O-methoxyethyl 5-nitroindole, 2'-O-methoxyethyl 4-nitrobenzimidazole, 2'-O-methoxyethyl 3-nitropyrrole, and combinations thereof. More preferably, the universal base is deoxyinosine, 1-(2'-deoxy-beta-D-ribofuranosyl)-3-nitropyrrole or 5-nitroindole, most preferably, deoxyinosine.

Preferably, the separation portion comprises contiguous nucleotides having at least three, more preferably at least four, most preferably at least five universal bases.

Preferably, in the DPO structure the 5'-first priming portion is longer than the 3'-second priming portion. The 5'-first priming portion is preferably 15-60 nucleotides, more preferably 15-40 nucleotides, still more preferably 15-25 nucleotides in length. It is preferable that the 3'-second priming portion is 3-15 nucleotides, more preferably 5-15 nucleotides, still more preferably 6-13 nucleotides in length. The separation portion is preferably 3-10 nucleotides, more preferably 4-8 nucleotides, most preferably 5-7 nucleotides in length. According to a preferred embodiment, the $T_m$ of the 5'-first priming portion ranges from 40° C. to 80° C., more preferably 45° C. to 65° C. The $T_m$ of the 3'-second priming portion ranges preferably from 10° C. to 40° C. It is preferable that the $T_m$ of the separation portion ranges from 3° C. to 15° C.

According to a preferred embodiment, the $T_m$ of the 3'-first priming portion ranges from 40° C. to 80° C., more preferably 45° C. to 65° C. The $T_m$ of the 5'-second priming portion ranges preferably from 10° C. to 40° C. It is preferable that the $T_m$ of the separation portion ranges from 3° C. to 15° C.

The conventional PCR technologies using primers for detecting target nucleic acid cannot be free from false signals at a satisfactory level due to inherent limitations of primers used. However, the primers having the DPO structure with such deliberative design are hybridized with the target nucleic acid sequence with a dramatically enhanced specificity, permitting to detect the target nucleic acid sequence with no false signals. As used herein, the term "conventional" in conjunction with primers means any primer not having DPO structure. They are described herein as conventional primers.

In accordance with another aspect of this invention, there is provided a kit for detecting a target nucleic acid sequence from a DNA or a mixture of nucleic acids by a cyclic exonucleolytic reaction, comprising:

(a) a probe having a hybridizing nucleotide sequence complementary to a first site on the target nucleic acid sequence, a fluorescent reporter molecule, and a quencher molecule capable of quenching the fluorescence of the reporter molecule; and (b) an enzyme having an exonuclease activity for cleavage of the probe.

Since the kit of this invention is constructed to perform the detection method of the present invention described above, the common descriptions between them are omitted in order to avoid undue redundancy leading to the complexity of this specification.

The present kits may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity.

The kits may also include reagents necessary for performing positive and negative control reactions. Optimal amounts of reagents to be used in a given reaction can be readily determined by the skilled artisan having the benefit of the current disclosure. The kits, typically, are adopted to contain the constituents afore-described in separate packaging or compartments.

The features and advantages of the present invention will be summarized as follows:

(a) The present invention is drawn to a novel approach to amplify signals indicating target nucleic acid sequences by cyclic exonuleolytic reactions (CER) comprising (i) signal generation by the cleavage of dual labeled probes by 5' to 3' or 3' to 5' exonuclease activity of an enzyme (preferably, 5' to 3' or 3' to 5' exonuclease activity of thermostable template-dependent nucleic acid polymerase) and (ii) signal amplification by repetition of hybridization and denaturation between dual labeled probes and the target nucleic acid sequence.

(b) Because the signal amplification in the CER method is accomplished irrespectively of amplification of target sequences, it is not necessary that amplification primers are used for signal amplification in the CER method.

(c) Because the present invention uses the 5' to 3' exonuclease activity of template-dependent nucleic acid polymerases being independent on primers and their extended products, it can amplify signals and detect target sequences with no help of additional primers for activation of the 5' to 3' exonuclease activity.

(d) The present CER method permits to detect target sequences using solely probes with no help of primers for signal generation or primers for target amplification. In these connections, the present invention can be free from shortcomings of conventional technologies associated with utilization of multiple oligonucleotides such as difficulties in sequence determination of oligonucleotides and optimization of reaction conditions and cost-ineffectiveness. In particular, the above-described advantages of the present invention become more highlighted in multiplex target detection.

(e) In the CER method using probes immobilized on a solid substrate, the repetition of hybridization and denaturation for cyclic exonucleolytic reactions enables most of the immobilized probes to be digested, thereby resulting in maximization of signal generation.

(f) Where the present invention is carried out using a thermostable template-dependent nucleic acid polymerase having the 5' to 3' exonuclease activity and an upstream primer together with a probe, it can generate signals indicating target sequences through two distinctly different 5' to 3' exonuclease activities of the template-dependent nucleic acid polymerase: (i) the 5' to 3' exonuclease activity being independent on interaction with either the upstream primer or an extended product of the upstream primer; and (ii) the 5' to 3' exonuclease activity being dependent on interaction with either the upstream primer or an extended product of the upstream primer.

(g) Alternatively, the present invention may be also performed using additional reverse primers for enhancement in its detection efficiency by increasing amounts of target sequences. Also, the present invention may be also carried out using a primer pair (a forward primer and a reverse primer) for target amplification.

(h) As discussed hereinabove, the primers used in the present invention having the DPO structure gives rise to the improvement in its binding specificity, thereby eliminating false positive signals associated with non-target binding of primers in real-time PCR reactions The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Evaluation of Cyclic Exonucleolytic Reaction for the Detection of a Target Nucleic Acid Sequence Using DNA Polymerase Having 5' to 3' Exonuclease Activity Cyclic exonucleolytic reaction of this invention was evaluated whether the cyclic exonucleolytic reaction can generate a signal sufficient to detect a target nucleic, acid sequence using a Taq DNA polymerase having 5' to 3' exonuclease activity.

To examine this evaluation, the synthetic oligonucleotides for *Staphylococcus aureus* gene and *Streptococcus pneumoniae* gene were used as templates. A dual-labeled probe has 6-FAM (6-carboxyfluorescein) as a fluorescent reporter molecule at its 5'-end and Black Hole quencher 1 (BHQ-1) as a quencher molecule at its internal sequence. The dual-labeled probe is modified by phosphorylation at its 3'-end, such that the dual-labeled probe is not extended. Cyclic exonucleolytic reactions were conducted using the Taq DNA polymerase having 5' to 3' exonuclease activity. The signals were measured at the hybridization step of each cycle.

A. Cyclic Exonucleolytic Reaction for the Detection of *S. aureus* Gene

When the target nucleic acid sequence of the *S. aureus* gene is used as a template, the sequences of the synthetic template and the dual-labeled probe used in this Example are:

```
SA_T70
                                                        (SEQ ID NO: 1)
5'-GGTGTAGGTGGTGGCGGTAACAACGCCGTAAACCGAATGATTGACCACGGAATGAATAATGTTGAA

TTTA-3'

SA_DLP
                                                        (SEQ ID NO: 2)
5'-[6-FAM]CATTCCG[T(BHQ-1)]GGTCAATCATTCGGTT[Phos]-3'
```

The cyclic exonucleolytic reaction was conducted in the final volume of 20 µl containing 0.2 pmole of synthetic template (SEQ ID NO: 1), 2 µl of 10× DiaStar™ Taq buffer, 2 units of DiaStar™ Taq DNA polymerase (Solgent, Korea), 5 mM of MgCl$_2$ and 5 pmole of dual-labeled probe (SEQ ID NO: 2); the tube containing the reaction mixture was placed in the real-time thermocycler (CFX96, Bio-Rad); the reaction mixture was denatured for 2 min at 95° C. and subjected to 40 cycles of 20 sec at 95° C. and 60 sec at 55° C. Detection of the generated signal was performed at the hybridization step (55° C.) of each cycle.

Figure 8:
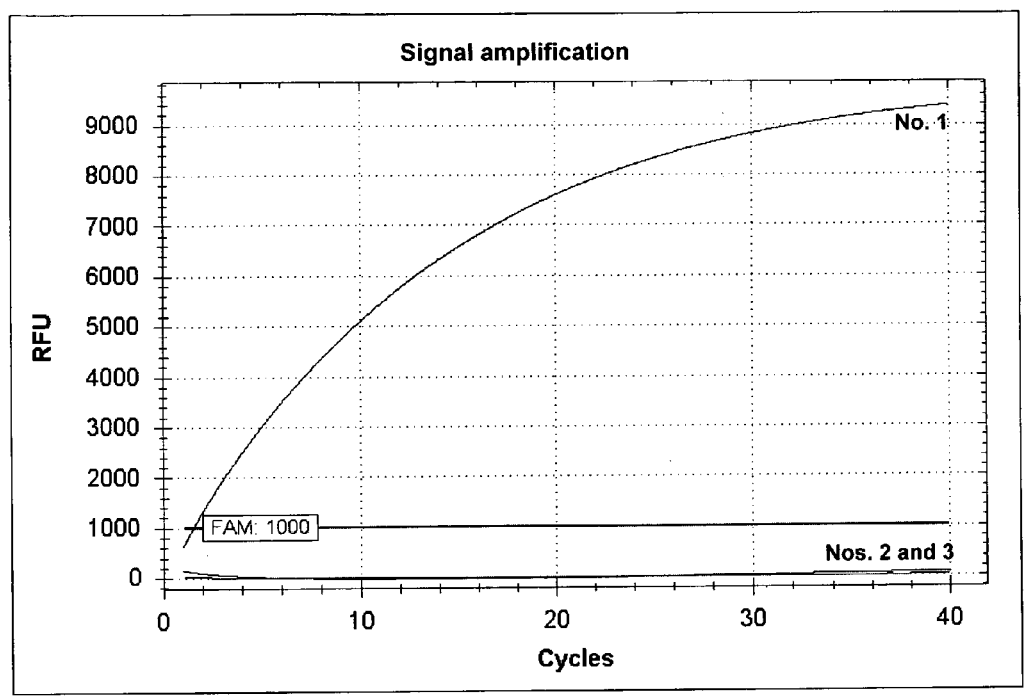
FIG. 8 shows the results of a cyclic exonucleolytic reaction using a Taq DNA polymerase having 5' to 3' exonuclease activity for the detection of *Staphylococcus aureus* gene.

As shown in FIG. 8, the target signal amplification for the detection of *S. aureus* gene was observed in the presence of the template (No. 1) but not observed in the absence of the template (No. 2) or the enzyme (No. 3). Therefore, it could be understood that cyclic exonucleolytic reaction can provide signals sufficient for detecting *S. aureus* gene through only the repetition of denaturation, hybridization and cleavage of the dual-labeled probe by 5' to 3' exonuclease activity of the Taq DNA polymerase.

B. Cyclic Exonucleolytic Reaction for the Detection of *S. pneumoniae* Gene

When the target nucleic acid sequence of the *S. pneumoniae* gene is used as a template, the sequences of the synthetic template and the dual-labeled probe used in this Example are:

SP_T105 (SEQ ID NO: 3)

5'-TTACTGAAAGACAATGAAGACAACCTAACAGGGGAAGATGTTCGCGAAGGCTTAACTGCAGTTATCT
CAGTTAAACACCCAAATCCACAGTTTGAAGGACAAACC-3'

SP_DLP (SEQ ID NO: 4)

5'-[6-FAM]TCCTTCAAACTGTGGATT[T(BHQ-1)]GGGTGT[Phos]-3'

The cyclic exonucleolytic reaction was conducted as the protocol used for *S. aureus*, except for template (0.2 pmole of *S. pneumoniae*) and dual-labeled probe (SEQ ID NO: 4)

Figure 9:
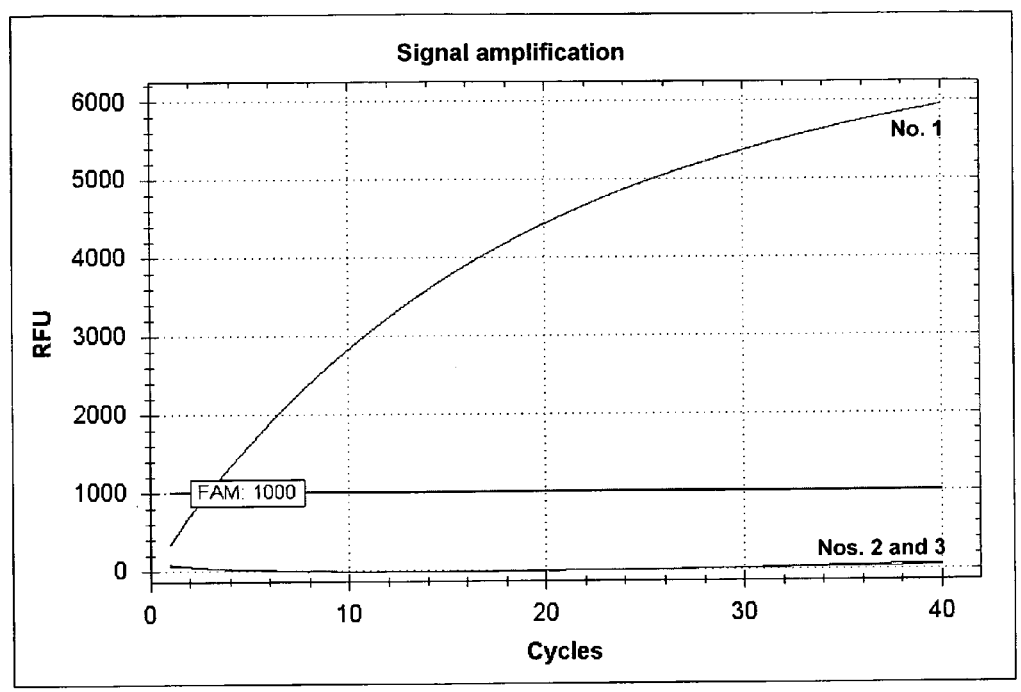
FIG. 9 shows the results of a cyclic exonucleolytic reaction using a Taq DNA polymerase having 5' to 3' exonuclease activity for the detection of *Streptococcus pneumoniae* gene.

As shown in FIG. 9, the target signal amplification for the detection of *S. pneumoniae* gene was observed in the presence of the template (No. 1) but not observed in the absence of the template (No. 2) or the enzyme (No. 3). Therefore, it could be understood that cyclic exonucleolytic reaction can provide signals sufficient for detecting *S. pneumoniae* gene through only the repetition of denaturation, hybridization and cleavage of the dual-labeled probe by 5' to 3' exonuclease activity of the Taq DNA polymerase.

Example 2

Evaluation of Cyclic Exonucleolytic Reaction for the Detection of *Neisseria gonorrhoeae* Gene Using DNA Polymerase Having 3' to 5' Exonuclease Activity We further examined whether a cyclic exonucleolytic reaction can amplify a signal sufficient to detect a target nucleic acid sequence using a Pfu DNA polymerase having 3' to 5' exonuclease activity.

To examine this evaluation, the synthetic oligonucleotide for *N. gonorrhoeae* gene was used as a template. A mismatch-carrying dual-labeled probe has a deoxyinosine as a mismatch nucleotide at its 3'-end. The probe is labeled with 6-FAM as a fluorescent reporter molecule at its 5'-end and Black Hole quencher 1 (BHQ-1) as a quencher molecule at its 3'-end. Cyclic exonucleolytic reactions were conducted using the Pfu DNA polymerase having 3' to 5' exonuclease activity. The signals were measured at the hybridization step of each cycle.

The sequences of the synthetic template and the mismatch-carrying dual-labeled probe used in this Example are:

NG-T70 (SEQ ID NO: 5)

5'-GAAACCAGTTCCGGCTGTTGTCGGCAAGCCGGGGTCGGATGTGTATTATGCCGGTCTGAATTACA
AAAAT-3'

NG_DLP (SEQ ID NO: 6)

5'-[BHQ-1]GACCCCGGCTTGCCGACAACI[6-FAM]-3'

The cyclic exonucleolytic reaction was conducted in the final volume of 20 μl containing 0.2 pmole of synthetic template (SEQ ID NO: 5), 2 μl of 10×PfuUltra™ II reaction buffer [containing 20 mM of MgCl₂], 1 unit of PfuUltra™ II fusion HS DNA polymerase (Stratagene, USA), 2.4 ul of 25 mM MgCl₂ and 5 pmole of mismatch-carrying dual-labeled probe (SEQ ID NO: 6); the tube containing the reaction mixture was placed in the real-time thermocycler (CFX96, Bio-Rad); the reaction mixture was denatured for 2 min at 95° C. and subjected to 40 cycles of 20 sec at 95° C. and 60 sec at 55° C. Detection of the generated signal was performed at the hybridization step (55° C.) of each cycle.

As shown in FIG. 10, the target signal amplification for the detection of *N. gonorrhoeae* gene was observed in the presence of the template (No. 1) but not observed in the absence of the template (No. 2) or the enzyme (No. 3). Therefore, it could be understood that cyclic exonucleolytic reaction can provide signals sufficient for detecting *N. gonorrhoeae* gene through only the repetition of denaturation, hybridization and cleavage of the mismatch-carrying dual-labeled probe by 3' to 5' exonuclease activity of the Pfu DNA polymerase.

Example 3

Cyclic Exonucleolytic Reaction for the Detection of *S. pneumoniae* Gene Using DNA Polymerase Having 5' to 3' Exonuclease Activity We applied a cyclic exonucleolytic reaction to detect a *S. pneumoniae* gene using DNA polymerase having 5' to 3' exonuclease activity.

For this application, the amplified products were obtained by using the genomic DNA of *S. pneumoniae* as a template and a pair of amplification primer (SEQ ID NOs: 7 and 8). The sequences of the dual-labeled probe and primers used in this Example are:

SP_F (SEQ ID NO: 7)

5'-GGTTTCCGTACAGCCTTGA-3'

SP_R (SEQ ID NO: 8)

5'-TTGACCACTTCGCTATTTCC-3'

-continued

SP_DLP (SEQ ID NO: 4)

5'-[6-FAM]TCCTTCAAACTGTGGATT[T(BHQ-1)]GGGTGT[Phos]-3'

A. Amplification of S. pneumoniae Gene

The amplification was conducted in the final volume of 20 μl containing 10 ng of S. pneumoniae genomic DNA, 2 μl of 10× DiaStar™ Taq buffer, 2 units of DiaStar™ Taq DNA polymerase (Solgent, Korea), 200 μM each of four dNTPs (dATP, dCTP, dGTP and dTTP), 5 mM of $MgCl_2$, 5 pmole of forward primer (SEQ ID NO: 7) and 5 pmole of reverse primer (SEQ ID NO: 8); the tube containing the reaction mixture was placed in the thermocycler (ABI9700, Applied BioSystems); the reaction mixture was denatured for 15 min at 95° C. and subjected to 40 cycles of 30 s at 94° C., 60 s at 55° C. and 60 s at 72° C. Amplified products were purified with PCR purification Kit (Solgent, Korea). Final elution volume of the purification step was 50 μl.

B. Cyclic Exonucleolytic Reaction

The cyclic exonucleolytic reaction was conducted in the final volume of 20 μl containing 5 μl of the purified PCR product, 2 μl of 10× DiaStar™ Taq buffer, 2 units of DiaStar™ Taq DNA polymerase (Solgent, Korea), 5 mM of $MgCl_2$ and 5 pmole of dual-labeled probe (SEQ ID NO: 4); the tube containing the reaction mixture was placed in the real-time thermocycler (CFX96, Bio-Rad); the reaction mixture was denatured for 2 min at 95° C. and subjected to 40 cycles of 20 sec at 95° C. and 60 sec at 55° C. Detection of the generated signal was performed at the hybridization step (55° C.) of each cycle.

Figure 11:
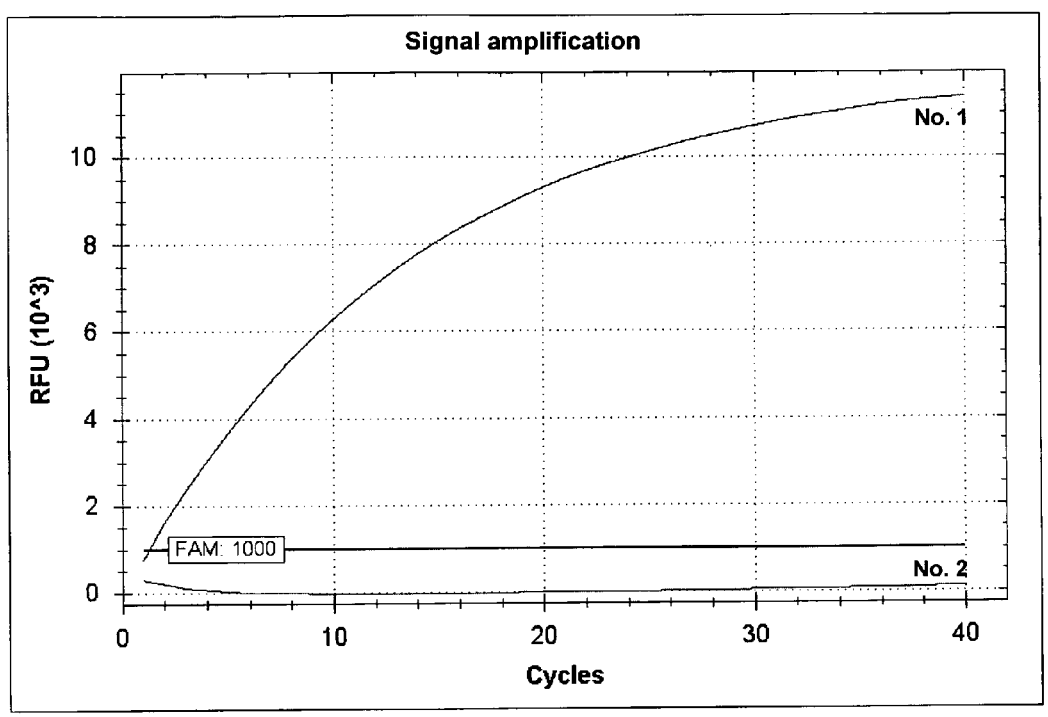
FIG. 11 shows the results of a cyclic exonucleolytic reaction using a Taq DNA polymerase having 5' to 3' exonuclease activity for the detection of *Streptococcus pneumoniae* gene. The amplified products of *S. pneumoniae* genomic DNA were used as a template.

As shown in FIG. 11, the target signal amplification for the detection of S. pneumoniae gene was observed in the presence of the template (No. 1) but not observed in the absence of the template (No. 2).

Example 4

Real-Time PCR Using Cyclic Exonucleolytic Reaction for the Detection of S. pneumoniae Gene We further applied the cyclic exonucleolytic reaction in real-time PCR for the detection of S. pneumoniae gene using Taq DNA polymerase having 5' to 3' exonuclease activity.

For this application, the amplified products were obtained by using the genomic DNA of S. pneumoniae as a template and a pair of amplification primer (SEQ ID NOs: 7 and 8).

To examine this evaluation, the genomic DNA of S. pneumoniae, primers (SEQ ID NOs: 7 and 8) and Taq DNA polymerase having 5' to 3' exonuclease activity were used.

The real-time PCR was conducted in the final volume of 20 μl containing 10 ng of S. pneumoniae genomic DNA, 2 μl of 10× DiaStar™ Taq buffer, 2 units of DiaStar™ Taq DNA polymerase (Solgent, Korea), 200 μM each of four dNTPs (dATP, dCTP, dGTP and dTTP), 5 mM of $MgCl_2$, 5 pmole of forward primer (SEQ ID NO: 7), 5 pmole of reverse primer (SEQ ID NO: 8) and 5 pmole of dual-labeled probe (SEQ ID NO: 4); the tube containing the reaction mixture was placed in the real-time thermocycler (CFX96, Bio-Rad); the reaction mixture was denatured for 2 min at 95° C. and subjected to 40 cycles of 20 sec at 95° C. and 60 sec at 55° C. Detection of the generated signal was performed at the hybridization step (55° C.) of each cycle.

Figure 12:
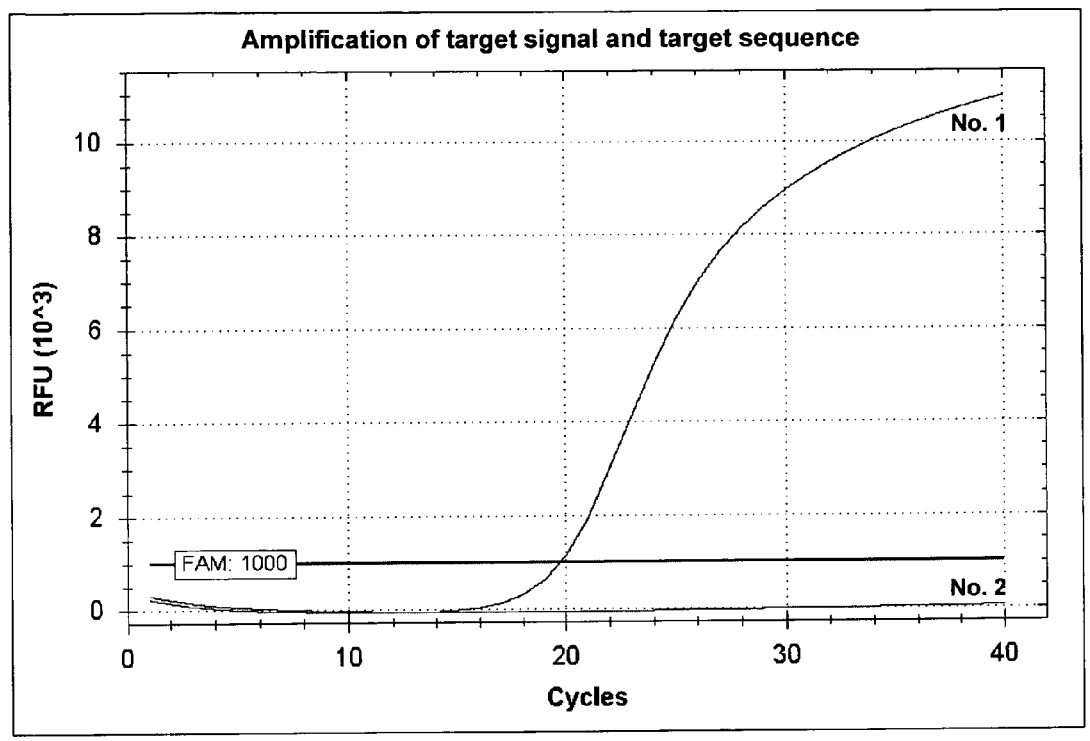
FIG. 12 shows the results of a cyclic exonucleolytic reaction with a primer pair using a Taq DNA polymerase having 5' to 3' exonuclease activity for the detection of *Streptococcus pneumoniae* gene.

As shown in FIG. 12, when the real-time PCR including the cyclic exonucleolytic reaction was conducted, the target signal for S. pneumoniae was observed in the presence of S. pneumoniae template (No. 1) but not observed in the absence of the template (No. 2).

Example 5

Evaluation of Cyclic Exonucleolytic Reaction for the Detection of Target Nucleic Acid Sequence on Chip We further examined whether the cyclic exonucleolytic reaction can amplify a signal sufficient to detect a target nucleic acid sequence in solid phase. To examine this evaluation, dual-labeled probes were immobilized on the surface of solid substrate.

A. Cyclic Exonucleolytic Reaction Using Taq DNA Polymerase Having 5' to 3' Exonuclease Activity on Chip A dual-labeled probe has amino group at its 3'-end and is immobilized on the surface of solid substrate through the amino group.

When the target nucleic acid sequence of S. aureus gene and Taq DNA polymerase having 5' to 3' exonuclease activity are used, the sequences of the synthetic template and the dual-labeled probe used in this Example are:

```
SA_T70
                                                         (SEQ ID NO: 1)
5'-GGTGTAGGTGGTGGCGGTAACAACGCCGTAAACCGAATGATTGACCACGGAATGAATAATGTTGA
ATTTA-3'

SA_DLP_S
                                                         (SEQ ID NO: 9)
5'-[BHQ-1]CATTCCGTGGTCAATCAT[T(fluorescein)]CGGTTTTTTT[AminoC7]-3'
```

The dual-labeled probe (SEQ ID NO: 9) was dissolved to a final concentration of 50 uM in Genorama Spotting Solution Type I. The dissolved dual-labeled probe was spotted onto glass slide (Genorama, Estonia) at room temperature and 70% relative humidity. The slide was incubated in a humid chamber at 37° C. for 2 hours. Then, the slide was soaked in 1% ammonium solution for 10 minutes, followed by washing with distilled water at room temperature.

The cyclic exonucleolytic reaction was conducted in the final volume of 20 μl containing 0.2 pmole of template (SEQ ID NO: 1), 2 μl of 10× DiaStar™ Taq buffer, 2 units of DiaStar™ Taq DNA polymerase (Solgent, Korea), 5 mM of $MgCl_2$; reaction mixture was transferred to the slide. The slide was placed in the in situ PCR machine (GeneAmp in situ, Perkin Elmer); the slide was denatured for 2 min at 95° C. and subjected to 40 cycles of 20 sec at 95° C. and 60 sec at 55° C. Following the cyclic exonucleolytic reaction, the slide was washed and detected through a microarray scanner (ScanArray4000, Perkin Elmer), followed by analysis of the images.

B. Cyclic Exonucleolytic Reaction Using Pfu DNA Polymerase Having 3' to 5' Exonuclease Activity on Chip A mismatch-carrying dual-labeled probe has amino group at its 5'-end and is immobilized on the surface of a solid substrate through the amino group. The mismatch-carrying dual-labeled probe has a deoxyinosine as a mismatch nucleotide.

When the target nucleic acid sequence of the N. gonorrhoeae gene and Pfu DNA polymerase having 3' to 5' exonuclease activity are used, the sequences of the synthetic template and the mismatch-carrying dual-labeled probe used in this Example are:

NG_T70
(SEQ ID NO: 5)
5'-GAAACCAGTTCCGGCTGTTGTCGGCAAGCCGGGGTCGGATGTGTATTATGCCGGTCTGAATTACA

AAAAT-3'

NG_DLP_S
(SEQ ID NO: 10)
5'-[AminoC6]TTTT[T(fluorescein)]GACCCCGGCTTGCCGACAACI[BHQ-1]-3'

The mismatch-carrying dual-labeled probe (SEQ ID NO: 10) was dissolved to a final concentration of 50 uM in Genorama Spotting Solution Type I. The dissolved mismatch-carrying dual-labeled probe was spotted onto glass slide (Genorama, Estonia) at room temperature and 70% relative humidity. The slide was incubated in a humid chamber at 37° C. for 2 hours. Then, the slide was soaked in 1% ammonium solution for 10 minutes, followed by washing with distilled water at room temperature.

The cyclic exonucleolytic reaction was conducted in the final volume of 20 μl containing 0.2 pmole of template (SEQ ID NO: 5), 2 μl of 10×PfuUltra™ II reaction buffer [containing 20 mM of $MgCl_2$], 1 unit of PfuUltra™ II fusion HS DNA polymerase (Stratagene, USA), 2.4 ul of 25 mM $MgCl_2$; reaction mixture was transferred to the slide. The slide was placed in the in situ PCR machine (GeneAmp in situ, Perkin Elmer); the slide was denatured for 2 min at 95° C. and subjected to 40 cycles of 20 sec at 95° C. and 60 sec at 55° C. Following the cyclic exonucleolytic reaction, the slide was washed and detected through a microarray scanner (ScanArray4000, Perkin Elmer), followed by analysis of the images.

Having described a preferred embodiment of the present invention, it is to be understood that variants and modifications thereof falling within the spirit of the invention may become apparent to those skilled in this art, and the scope of this invention is to be determined by appended claims and their equivalents.

---

What is claimed is:

1. A method for detecting a target nucleic acid sequence in a DNA molecule or a mixture of nucleic acids by a cyclic exonucleolytic reaction without the use of an upstream primer, which comprises the steps of:
   (a) hybridizing the target nucleic acid sequence with a probe, wherein the probe has a hybridizing nucleotide sequence complementary to a site on the target nucleic acid sequence, a fluorescent reporter molecule, and a quencher molecule capable of quenching the fluorescence of the reporter molecule;
   (b) contacting the target-hybridized probe with a template-dependent nucleic acid polymerase having 5' to 3' exonuclease activity for cleavage of the probe without the use of an upstream primer, such that either the fluorescent reporter molecule or the quencher molecule is released from the probe to unquench the fluorescence of the reporter molecule and generate a fluorescent signal indicative of the presence of the target nucleic acid sequence; wherein the probe is cleaved by the 5' to 3' exonuclease activity of the template-dependent nucleic acid polymerase that is independent from interaction with either an upstream primer or an extended product of an upstream primer;
   (c) denaturing a duplex of the probe-target nucleic acid sequence of step (b);
   (d) repeating the steps (a)-(c) at least twice to amplify the signal indicative of the presence of the target nucleic acid sequence; and
   (e) detecting the signal indicative of the presence of the target nucleic acid sequence, wherein the detection is performed for each cycle of the repetition of step (d), at the end of the repetition of step (d) or at each of predetermined time intervals during the repetition, such that the signal is indicative of the presence of the target nucleic acid sequence.

2. The method according to claim 1, wherein the polymerase having a 5' to 3' exonuclease activity is thermostable.

3. The method according to claim 2, wherein the method is performed on a solid phase and the probe is immobilized through its 3'-end on the surface of a solid substrate; wherein the probe has a digested portion and an undigested portion by the 5' to 3' exonuclease activity of the enzyme such that the undigested portion remains attached to the surface of the solid substrate; wherein the fluorescent reporter molecule on the probe is positioned on the undigested portion and the quencher molecule capable of quenching the fluorescence of the reporter molecule is positioned on the digested portion; wherein when the probe is hybridized with the target nucleic acid sequence, the digested portion of the probe is released from the probe by the 5' to 3' exonuclease activity of the polymerase and the fluorescence of the reporter molecule on the undigested portion of the probe is unquenched, whereby a fluorescent signal on the solid substrate is detected to determine the presence of the target nucleic acid sequence.

4. The method according to claim 1, wherein the probe has a match nucleotide sequence at its 5'-end.

5. The method according to claim 1, wherein the step (a) is performed using a reverse primer to produce the target nucleic acid sequence hybridizable with the probe in step (b) by an extension reaction of the reverse primer by the template-dependent nucleic acid polymerase.

6. The method according to claim 1, wherein the target nucleic acid sequence comprises at least two types of nucleic acid sequences and the probe comprises at least two types of probes.

* * * * *

SEQUENCE LISTING

```
<160> NUMBER OF SEQ ID NOS: 10

<210> SEQ ID NO 1
<211> LENGTH: 70
<212> TYPE: DNA
<213> ORGANISM: Artificial Sequence
<220> FEATURE:
<223> OTHER INFORMATION: synthetic template

<400> SEQUENCE: 1
ggtgtaggtg gtggcggtaa caacgccgta aaccgaatga ttgaccacgg aatgaataat    60
gttgaattta                                                           70

<210> SEQ ID NO 2
<211> LENGTH: 24
<212> TYPE: DNA
<213> ORGANISM: Artificial Sequence
<220> FEATURE:
<223> OTHER INFORMATION: Probe

<400> SEQUENCE: 2
cattccgtgg tcaatcattc ggtt                                           24

<210> SEQ ID NO 3
<211> LENGTH: 105
<212> TYPE: DNA
<213> ORGANISM: Artificial Sequence
<220> FEATURE:
<223> OTHER INFORMATION: synthetic template

<400> SEQUENCE: 3
ttactgaaag acaatgaaga caacctaaca ggggaagatg ttcgcgaagg cttaactgca    60
gttatctcag ttaaacaccc aaatccacag tttgaaggac aaacc                    105

<210> SEQ ID NO 4
<211> LENGTH: 25
<212> TYPE: DNA
<213> ORGANISM: Artificial Sequence
<220> FEATURE:
```

```
<223> OTHER INFORMATION: Probe

<400> SEQUENCE: 4
tccttcaaac tgtggatttg ggtgt                                          25

<210> SEQ ID NO 5
<211> LENGTH: 70
<212> TYPE: DNA
<213> ORGANISM: Artificial Sequence
<220> FEATURE:
<223> OTHER INFORMATION: synthetic template

<400> SEQUENCE: 5
gaaaccagtt ccggctgttg tcggcaagcc ggggtcggat gtgtattatg ccggtctgaa    60
ttacaaaaat                                                           70

<210> SEQ ID NO 6
<211> LENGTH: 21
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (21)..(21)
<223> OTHER INFORMATION: n denotes deoxyinosine

<400> SEQUENCE: 6
gaccccggct tgccgacaac n                                              21

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
ggtttccgta cagccttga                                                 19

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ttgaccactt cgctatttcc                                                20

<210> SEQ ID NO 9
<211> LENGTH: 29
<212> TYPE: DNA
<213> ORGANISM: Artificial Sequence
<220> FEATURE:
<223> OTHER INFORMATION: Probe

<400> SEQUENCE: 9
cattccgtgg tcaatcattc ggttttttt                                      29

<210> SEQ ID NO 10
<211> LENGTH: 26
<212> TYPE: DNA
<213> ORGANISM: Artificial Sequence
<220> FEATURE:
<223> OTHER INFORMATION: Probe
```

```
<220> FEATURE:
<221> NAME/KEY: misc_feature
<222> LOCATION: (26)..(26)
<223> OTHER INFORMATION: n denotes deoxyinosine

<400> SEQUENCE: 10
tttttgaccc cggcttgccg acaacn                                              26
```